(12) United States Patent
Althaus et al.

(10) Patent No.: US 6,905,687 B2
(45) Date of Patent: Jun. 14, 2005

(54) HUMAN PROCALCITONIN AND THE PREPARATION AND USE THEREOF

(75) Inventors: Harald Althaus, Wetter (DE); Hans-Peter Hauser, Marburg (DE)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 10/394,058

(22) Filed: Mar. 24, 2003

(65) Prior Publication Data

US 2003/0181662 A1 Sep. 25, 2003

Related U.S. Application Data

(62) Division of application No. 09/742,373, filed on Dec. 22, 2001, now Pat. No. 6,562,946.

(30) Foreign Application Priority Data

| Dec. 22, 1999 | (DE) | 199 62 434 |
| Apr. 3, 2000 | (DE) | 100 16 278 |
| Jun. 8, 2000 | (DE) | 100 27 954 |

(51) Int. Cl.$^7$ ................. C07K 14/585; C07K 14/435; A61K 38/23; G01N 33/53

(52) U.S. Cl. ................. 424/185.1; 424/192.1; 514/12; 435/7.1; 436/501; 530/356

(58) Field of Search ............ 530/350; 514/12; 424/185.1, 192.1; 436/501; 435/7.1

(56) References Cited

U.S. PATENT DOCUMENTS

| 3,057,782 A | 10/1962 | Lindner et al. | |
| 3,996,345 A | 12/1976 | Ullman et al. | |
| 5,340,716 A | 8/1994 | Ullman et al. | |
| 5,545,834 A | 8/1996 | Singh et al. | |
| 5,740,800 A | 4/1998 | Hendrickson et al. | 128/630 |
| 5,915,240 A | 6/1999 | Karpf | 705/2 |
| 5,993,811 A | 11/1999 | Becker et al. | 425/130.1 |

FOREIGN PATENT DOCUMENTS

| DE | 1155134 | 6/1958 | |
| DE | 198 47 690 A1 | 4/2000 | |
| DE | 199 03 336 A1 | 8/2000 | |
| EP | 0 080 614 A2 | 11/1982 | |
| EP | 0 227 054 B1 | 12/1986 | |
| EP | 0 246 446 B1 | 4/1987 | |
| EP | 0 411 945 A2 | 8/1990 | |
| EP | 0 515 194 A2 | 5/1992 | |
| EP | 0 656 121 B1 | 8/1993 | |
| EP | 0 997 735 A2 | 9/1999 | |
| EP | 1 026 506 A1 | 1/2000 | |
| EP | 1 111 050 A2 * | 6/2001 | C12N/15/16 |
| WO | WO 98/33524 | 1/1988 | |
| WO | WO 95/06877 | 3/1995 | |
| WO | WO 95/25172 | 9/1995 | |

OTHER PUBLICATIONS

Rehli et al (BBRC 226: 420–425, 1996).*
Snider et al (Journal of Investigative Medicine 45:552–560, 1997).*
Le Moullec et al (FEBS Lett. 167:93–97, 1984).*
Dialog (R) File 351: English Abstract of EP 1 026 506 A1.
Dialog (R) File 351: English Abstract of EP 0 997 735 A2.
S. Wrenger et al., "Amino–terminal Truncation of Procalcitonin, a Marker for Systemic Bacterial Infections, by Dipeptidyl Peptidase IV (DP IV), 2000" *Federation of European Biochemical Societies Letters*, 466, No. 1, (2000), pp. 155–159.
Xiao–Quing Liu et al., "A Novel Method for Increasing Production of Mature Proteins in the Periplasm of *Escherichia coli*," *Protein Science* (*1999*), vol. 8, 1999, Cambridge University Press, The Protein Society, pp. 2085–2089.
Rainer Fischer et al., "Molecular Farming of Recombinant Antibodies in Plants," *Biol. Chem.*, vol. 380, Jul./Aug. 1999, pp. 825–839.
Eric S. Nylen, et al., "Mortality is increased by Procalcitonin and Decreased by an Antiserum Reactive to Procalcitonin in Experimental Sepsis," *Crit. Care Med.* 1998, vol. 26, No. 6, pp. 1001–1006.
W. Karzai et al., "Procalcitonin—A New Indicator of the Systemic Response to Severe Infections," Infection, 6, *A Journal of Infectious Disease—Clinical Study and Treatment*, vol. 25, 1997, pp. 329–334.
Michael Rehli et al., "Molecular Cloning and Expression of Mouse Procalcitonin," *Biochemical and Biophysical Research Communications* 226, pp. 420–425 (1996).
Edwin F. Ullman et al., "Luminescent Oxygen Channeling Assay (LOCI™): Sensitive, Broadly Applicable Homogeneous Immunoassay Method," *Clinical Chemistry*, vol. 42, No. 9, 1996, pp. 1518–1526.
Keith M. Thompson et al., "The Efficient Production of Stable, Human Monoclonal Antibody–Secreting Hybridomas from EBV–transformed Lymphocytes Using the Mouse Myeloma X63–Ag8.653 as a Fusion Partner," *Journal of Immunological Methods*, vol. 94, 1996, pp. 7–12.
Sebastian Messerschmid, "Erzeugung von Polyklonalen Antikörpen in Nicht–Säugern," *BIOforum*, Nov. 1996, pp. 500–502.

(Continued)

Primary Examiner—Mary E. Mosher
(74) Attorney, Agent, or Firm—Finnegan, Henderson, Farabow, Garrett and Dunner, L.L.P.

(57) ABSTRACT

The invention relates to human procalcitonin and the preparation and use thereof. In particular, a process for preparing human procalcitonin is described wherein a gene coding for a polypeptide comprising the amino acid sequence of human procalcitonin is inserted into a vector; a host organism is transformed with this gene-containing vector; and the polypeptide expressed by the host organism is isolated. Furthermore the use of the polypeptides according to the invention, in particular as medicaments and diagnostic agents is described.

16 Claims, 6 Drawing Sheets

OTHER PUBLICATIONS

Edwin F. Ullman et al., "Luminescent Oxygen Channeling Immunoassay: Measurement of Particle Binding Kinetics by Chemiluminescence," *Proc. Natl. Acad. Sci, USA,* vol. 91, 1994, pp. 5426–5430.

Gérard Mathis, "Rare Earth Cryptates and Homogeneous Fluoroimmunoassays with Human Sera," *Clin. Chem.,* vol. 39, No. 9, 1993, pp. 1953–1959.

Andrew Hiatt et al., "Assembly of Antibodies and Mutagenized Variants in Transgenic Plants and Plant Cell Cultures," *Genetic Engineering,* vol. 14, 1992, pp. 49–64.

James W. Larrick et al., "Recombinant Antibodies," *Review,* vol. 2, 1991, pp. 172–189.

J. Michael Conlon et al., "Structural Characterization of a High Molecular–mass Form of Calcitonin [procalcitonin–(60–116)–peptide] and Its Corresponding N–terminal Flanking Peptide [procalcitonin–(1–57)–peptide] in a Human Medullary Thyroid Carcinorma," *Biochem.,* vol. 256, 1988, pp. 245–250.

Pascale P. Ghillani et al., "Identification and Measurement of Calcitonin Precursors in Serum of Patients with Malignant Diseases," *Cancer Research,* vol. 49, 1989, pp. 6845.

Pascale Ghillani et al., "Monoclonal Antipeptide Antipeptide Antibodies As Tools To Dissect Closely Related Gene Products," *The Journal of Immunology,* vol. 141, 1988, pp. 3156–3163.

M. Philip Bailey et al., "On the Use of Fluorescent Labels in Immunoassay," *Journal of Pharmaceutical & Biomedical Analysis,* vol. 5, 1987, pp. 649–658.

Kazuaki Kitano et al., "Production of Human Monoclonal Antibodies by Heterohybridomas," *Appl Microbiol Biotechnol,* vol. 24, 1986, pp. 282–286.

Sidney Udenfriend et al., "Scintillation Proximity Radioimmunoassay Utilizing $^{125}$I–labeled Ligands," *Proc. Natl. Acad. Sci, USA,* vol. 82, 1985, pp. 8672–8676.

Moullec et al., "The Complete Sequence of Human Preprocalcitonin," *Federation of European Biochemical Societies,* vol. 167, 1984, pp. 93–97.

R.C. Boguslaski et al., "Homogeneous Immunoassays," *Applied Biochemistry and Biotechnology,* vol. 7, 1982, pp. 401–414.

\* cited by examiner

FIG 1

APFRSALESS PADPATLSED EARLLLAALV QDYVQMKASE LEQEQEREGS

SLDSPRSKRC GNLSTCMLGT YTQDFNKFHT FPQTAIGVGA PGKKRDMSSD

LERDHRPHVS MPQNAN

FIG 2A

APFRSALESS PADPATLSED EARLRLAALV QDYVQMKASE LEQEQEREGS

SLDSPRSKRC GNLSTCMLGT YTQDFNKFHT FPQTAIGVGA PGKKRDMSSD

LERDHRPHVS MPQNAN

FIG 2B

MRGSHHHHHGS

APFRSALESS PADPATLSED EARLRLAALV QDYVQMKASE LEQEQEREGS

SLDSPRSKRC GNLSTCMLGT YTQDFNKFHT FPQTAIGVGA PGKKRDMSSD

LERDHRPHVS MPQNAN

```
  1 CTCGAGAAAT CATAAAAAAT TTATTTGCTT TGTGAGCGGA TAACAATTAT

51 AATAGATTCA ATTGTGAGCG GATAACAATT TCACACAGAA TTCATTAAAG

101 AGGAGAAATT AACTATGAGA GGATCGCATC ACCATCACCA TCACGGATCC

151 GCATGCGAGC TCGGTACCCC GGGTCGACCT GCAGCCAAGC TTAATTAGCT

201 GAGCTTGGAC TCCTGTTGAT AGATCCAGTA ATGACCTCAG AACTCCATCT

251 GGATTTGTTC AGAACGCTCG GTTGCCGCCG GGCGTTTTTT ATTGGTGAGA

301 ATCCAAGCTA GCTTGGCGAG ATTTTCAGGA GCTAAGGAAG CTAAAATGGA

351 GAAAAAAATC ACTGGATATA CCACCGTTGA TATATCCCAA TGGCATCGTA

401 AAGAACATTT TGAGGCATTT CAGTCAGTTG CTCAATGTAC CTATAACCAG

451 ACCGTTCAGC TGGATATTAC GGCCTTTTTA AAGACCGTAA AGAAAAATAA

501 GCACAAGTTT TATCCGGCCT TTATTCACAT TCTTGCCCGC CTGATGAATG

551 CTCATCCGGA ATTTCGTATG GCAATGAAAG ACGGTGAGCT GGTGATATGG

601 GATAGTGTTC ACCCTTGTTA CACCGTTTTC CATGAGCAAA CTGAAACGTT

651 TTCATCGCTC TGGAGTGAAT ACCACGACGA TTTCCGGCAG TTTCTACACA

701 TATATTCGCA AGATGTGGCG TGTTACGGTG AAAACCTGGC CTATTTCCCT

751 AAAGGGTTTA TTGAGAATAT GTTTTTCGTC TCAGCCAATC CCTGGGTGAG

801 TTTCACCAGT TTTGATTTAA ACGTGGCCAA TATGGACAAC TTCTTCGCCC

851 CCGTTTTCAC CATGGGCAAA TATTATACGC AAGGCGACAA GGTGCTGATG

901 CCGCTGGCGA TTCAGGTTCA TCATGCCGTC TGTGATGGCT TCCATGTCGG

951 CAGAATGCTT AATGAATTAC AACAGTACTG CGATGAGTGG CAGGGCGGGG
```

FIG. 3A

```
1001 CGTAATTTTT TTAAGGCAGT TATTGGTGCC CTTAAACGCC TGGGGTAATG

1051 ACTCTCTAGC TTGAGGCATC AAATAAAACG AAAGGCTCAG TCGAAAGACT

1101 GGGCCTTTCG TTTTATCTGT TGTTTGTCGG TGAACGCTCT CCTGAGTAGG

1151 ACAAATCCGC CGCTCTAGAG CTGCCTCGCG CGTTTCGGTG ATGACGGTGA

1201 AAACCTCTGA CACATGCAGC TCCCGGAGAC GGTCACAGCT TGTCTGTAAG

1251 CGGATGCCGG GAGCAGACAA GCCCGTCAGG GCGCGTCAGC GGGTGTTGGC

1301 GGGTGTCGGG GCGCAGCCAT GACCCAGTCA CGTAGCGATA GCGGAGTGTA

1351 TACTGGCTTA ACTATGCGGC ATCAGAGCAG ATTGTACTGA GAGTGCACCA

1401 TATGCGGTGT GAAATACCGC ACAGATGCGT AAGGAGAAAA TACCGCATCA

1451 GGCGCTCTTC CGCTTCCTCG CTCACTGACT CGCTGCGCTC GGTCTGTCGG

1501 CTGCGGCGAG CGGTATCAGC TCACTCAAAG GCGGTAATAC GGTTATCCAC

1551 AGAATCAGGG GATAACGCAG GAAAGAACAT GTGAGCAAAA GGCCAGCAAA

1601 AGGCCAGGAA CCGTAAAAAG GCCGCGTTGC TGGCGTTTTT CCATAGGCTC

1651 CGCCCCCCTG ACGAGCATCA CAAAAATCGA CGCTCAAGTC AGAGGTGGCG

1701 AAACCCGACA GGACTATAAA GATACCAGGC GTTTCCCCCT GGAAGCTCCC

1751 TCGTGCGCTC TCCTGTTCCG ACCCTGCCGC TTACCGGATA CCTGTCCGCC

1801 TTTCTCCCTT CGGGAAGCGT GGCGCTTTCT CAATGCTCAC GCTGTAGGTA

1851 TCTCAGTTCG GTGTAGGTCG TTCGCTCCAA GCTGGGCTGT GTGCACGAAC

1901 CCCCCGTTCA GCCCGACCGC TGCGCCTTAT CCGGTAACTA TCGTCTTGAG

1951 TCCAACCCGG TAAGACACGA CTTATCGCCA CTGGCAGCAG CCACTGGTAA

2001 CAGGATTAGC AGAGCGAGGT ATGTAGGCGG TGCTACAGAG TTCTTGAAGT
```

*FIG. 3B*

```
2051 GGTGGCCTAA CTACGGCTAC ACTAGAAGGA CAGTATTTGG TATCTGCGCT

2101 CTGCTGAAGC CAGTTACCTT CGGAAAAAGA GTTGGTAGCT CTTGATCCGG

2151 CAAACAAACC ACCGCTGGTA GCGGTGGTTT TTTTGTTTGC AAGCAGCAGA

2201 TTACGCGCAG AAAAAAAGGA TCTCAAGAAG ATCCTTTGAT CTTTTCTACG

2251 GGGTCTGACG CTCAGTGGAA CGAAAACTCA CGTTAAGGGA TTTTGGTCAT

2301 GAGATTATCA AAAAGGATCT TCACCTAGAT CCTTTTAAAT TAAAAATGAA

2351 GTTTTAAATC AATCTAAAGT ATATATGAGT AAACTTGGTC TGACAGTTAC

2401 CAATGCTTAA TCAGTGAGGC ACCTATCTCA GCGATCTGTC TATTTCGTTC

2451 ATCCATAGCT GCCTGACTCC CCGTCGTGTA GATAACTACG ATACGGGAGG

2501 GCTTACCATC TGGCCCCAGT GCTGCAATGA TACCGCGAGA CCCACGCTCA

2551 CCGGCTCCAG ATTTATCAGC AATAAACCAG CCAGCCGGAA GGGCCGAGCG

2601 CAGAAGTGGT CCTGCAACTT TATCCGCCTC CATCCAGTCT ATTAATTGTT

2651 GCCGGGAAGC TAGAGTAAGT AGTTCGCCAG TTAATAGTTT GCGCAACGTT

2701 GTTGCCATTG CTACAGGCAT CGTGGTGTCA CGCTCGTCGT TTGGTATGGC

2751 TTCATTCAGC TCCGGTTCCC AACGATCAAG GCGAGTTACA TGATCCCCCA

2801 TGTTGTGCAA AAAAGCGGTT AGCTCCTTCG GTCCTCCGAT CGTTGTCAGA

2851 AGTAAGTTGG CCGCAGTGTT ATCACTCATG GTTATGGCAG CACTGCATAA

2901 TTCTCTTACT GTCATGCCAT CCGTAAGATG CTTTTCTGTG ACTGGTGAGT

2951 ACTCAACCAA GTCATTCTGA GAATAGTGTA TGCGGCGACC GAGTTGCTCT

3001 TGCCCGGCGT CAATACGGGA TAATACCGCG CCACATAGCA GAACTTTAAA

3051 AGTGCTCATC ATTGGAAAAC GTTCTTCGGG GCGAAAACTC TCAAGGATCT
```

FIG. 3C

3101 TACCGCTGTT GAGATCCAGT TCGATGTAAC CCACTCGTGC ACCCAACTGA

3151 TCTTCAGCAT CTTTTACTTT CACCAGCGTT TCTGGGTGAG CAAAAACAGG

3201 AAGGCAAAAT GCCGCAAAAA AGGGAATAAG GGCGACACGG AAATGTTGAA

3251 TACTCATACT CTTCCTTTTT CAATATTATT GAAGCATTTA TCAGGGTTAT

3301 TGTCTCATGA GCGGATACAT ATTTGAATGT ATTTAGAAAA ATAAACAAAT

3351 AGGGGTTCCG CGCACATTTC CCCGAAAAGT GCCACCTGAC GTCTAAGAAA

3401 CCATTATTAT CATGACATTA ACCTATAAAA ATAGGCGTAT CACGAGGCCC

3451 TTTCGTCTTC AC

FIG. 3D

1 GGATCCGCAC CATTCAGGTC TGCCCTGGAG AGCAGCCCAG CAGACCCGGC

51 CACGCTCAGT GAGGACGAAG CGCGCCTCC GGCTGGCTGC ACTGGTGCAG

101 GACTATGTGC AGATGAAGGC CAGTGAGCTG GAGCAGGAGC AAGAGAGAGA

151 GGGCTCCAGC CTGGACAGCC CCAGATCTAA GCGGTGCGGT AATCTGAGTA

201 CTTGCATGCT GGGCACATAC ACGCAGGACT TCAACAAGTT TCACACGTTC

251 CCCCAAACTG CAATTGGGGT TGGAGCACCT GGAAAGAAAA GGGATATGTC

301 CAGCGACTTG GAGAGAGACC ATCGCCCTCA TGTTAGCATG CCCCAGAATG

351 CCAACTAAAA GCTT

```
  1       GCAC CATTCAGGTC TGCCCTGGAG AGCAGCCCAG CAGACCCGGC

51 CACGCTCAGT GAGGACGAAG CGCGCCTCC  TGCTGGCTGC ACTGGTGCAG

101 GACTATGTGC AGATGAAGGC CAGTGAGCTG GAGCAGGAGC AAGAGAGAGA

151 GGGCTCCAGC CTGGACAGCC CCAGATCTAA GCGGTGCGGT AATCTGAGTA

201 CTTGCATGCT GGGCACATAC ACGCAGGACT TCAACAAGTT TCACACGTTC

251 CCCCAAACTG CAATTGGGGT TGGAGCACCT GGAAAGAAAA GGGATATGTC

301 CAGCGACTTG GAGAGAGACC ATCGCCCTCA TGTTAGCATG CCCCAGAATG

351 CCAACTAA
```

HUMAN PROCALCITONIN AND THE PREPARATION AND USE THEREOF

This is a division of application Ser. No. 09/742,373, filed Dec. 22, 2000, now U.S. Pat. No. 6,562,946 issued May 13, 2003, and which is incorporated herein by reference.

The invention relates to human procalcitonin and the preparation, in particular by genetic engineering processes, and use thereof.

Procalcitonin ("pCT") is a protein consisting of 116 amino acids and having a molecular weight of about 13,000 dalton. It is the prohormone of calcitonin which under normal metabolic conditions is produced and secreted by the C cells of the thyroid. pCT and calcitonin synthesis is initiated by translation of preprocalcitonin ("pre-pCT"), a precursor peptide comprising 141 amino acids. The amino acid sequence of human pre-pCT was described by Moullec et al. in FEBS Letters, 167:93–97 in 1984. pCT is formed after cleavage of the signal peptide (first 25 amino acids of pre-pCT). In healthy people the hormone calcitonin (amino acids 60–91 of the pCT amino acid sequence), and N-procalcitonin (amino acids 1–57 of the pCT amino acid sequence) and katacalcin (amino acids 96–116 of the pCT amino acid sequence) are produced intracellularly from pCT by specific proteolysis (see also Conlan et al. (1988) Biochem. J., 256:245–250). pCT and fragments thereof were detected in increased concentrations in the serum or plasma of patients, in particular in cases of certain neoplastic diseases (Ghillani et al. (1989) Cancer Research, 49:6845–6851) and sepsis (EP-B1-0 656 121) and SIRS (systemic inflammatory response syndrome) (Snider et al., (1997) J. Investig. Med., 45:552–560).

During the typical sepsis bacteria are released continuously or in phases from a focus into the bloodstream. Endotoxin or other pyrogenic and toxic substances interacting with body mechanisms cause the clinical manifestations. The acute onset triggers chills and in severe cases a shock reaction. Special forms of septic shock are Waterhouse-Friderichsen syndrome and toxic shock syndrome (TSS). TSS is known as an acute clinical picture in staphylococcal infections which is caused by a specific staphylococcal toxin. A severe sepsis quite frequently develops in patients with serious primary disorders such as, for example, neoplastic diseases, serious burns and traumas.

The importance for sepsis diagnosis of detecting pathogens in the blood ("positive blood culture, bacteremia") has been pushed into the background, because in general the blood culture is positive only in 20 to 40% of sepsis cases. The term sepsis has therefore undergone a change. The modern term "sepsis" describes a clinical syndrome which in general comprises fever, leukocytosis, alterations of consciousness, a hyperdynamic circulation ("warm shock") and a hypermetabolic state, a positive blood culture no longer being required as a prerequisite for sepsis diagnosis.

WO 98/33524 suggests employing antibodies binding to pCT for the therapy of sepsis and SIRS.

Over many years polyclonal antibodies were obtained from immunization by calcitonin and used for detecting so-called immunoreactive calcitonin which aside from calcitonin also comprises procalcitonin and further procalcitonin fragments. Immunization by synthetic peptides having amino acid sequences corresponding to the sequences of procalcitonin segments succeeded in producing various monoclonal antibodies binding to various calcitonin and katacalcin epitopes (Ghillani et al. (1988) J. Immunol., 141:3156–3163).

On the basis of these antibodies sandwich immunoassays for detecting pCT and calcitonin in serum samples were also developed. A combination of an anti-katacalcin antibody and an anti-calcitonin antibody was suggested for detecting calcitonin precursor molecules. A synthetic peptide suited to these antibodies was employed as standard material.

It is known that in immunochemical tests the measured signals for standards and samples need not necessarily be identical even if the amount of antigen is exactly the same. If standard and sample antigens are not really identical regarding their immunochemical reactivity, the antibodies employed in the test will recognize either the one or the other antigen better. This leads in the end to different measured signals for samples and standards.

It follows from this that the use as standard antigen of antigen fragments instead of the whole protein is often associated with disadvantages and can, in particular, lead to distorted measurements. Furthermore, it is in general not possible for the epitopes based on the three-dimensional structure of the correctly folded protein to be correctly represented by shorter peptides. This results in it not being possible to obtain antibodies against such conformation epitopes on use of peptides as immunogens. It is advantageous especially in competitive test formats if the substance to be detected has the same immunochemical reactivity as the corresponding solid phase or label-bound test reagent.

Although the complete amino acid sequence of human pCT has now been known since 1984, so far human pCT has not been prepared successfully, in particular not in relatively large amounts and reproducibly. So far only murine pCT could be expressed in E. coli by means of genetic engineering processes (Rehli et al. (1996) Biochem. Biophys. Res. Com., 226:420–425).

However, murine pCT differs from human pCT to such an extent (about 77% homology at the amino acid level) that it is still an object for the skilled worker to develop a process by which human pCT can be produced in relatively large amounts, cost effectively and in isolated form in order to be able to employ it particularly as an immunogen and/or standard and control sera antigen.

This object is achieved by providing the polypeptides according to the invention described in claims 1–3, the plasmids according to the invention described in claims 10 and 11, the cells according to the invention described in claim 12 and the preparation processes according to the invention described in claims 4–9. The polypeptides according to the invention, i.e. the polypeptides as claimed in one of claims 1–3 or the products of a process as claimed in claims 4–9, can be employed usefully in particular in the fields of diagnosis and therapy. Preferred embodiments of the invention are disclosed in claims 13–23. Furthermore, the polypeptides according to the invention can be used for immunization to obtain the antibodies according to the invention. A further embodiment of the invention is the pCT solutions described in claims 24–29.

It was not possible to predict the feasibility of human pCT expression according to the invention: pCT is expressed in the cell not as pCT, but originates from preprocalcitonin by proteolytic cleavage of the N-terminal signal peptide. It had to be assumed that in eukaryotes pCT without signal peptide is not expressed in the natural cell compartment and folds in a different way, potentially causing biological inactivation and possibly even instability. In addition, the heterologous expression in E. coli instead of the natural expression in animal cells and the expression attempted within the framework of the invention of a fusion protein of procalcitonin and the artificial sequence MRSHHHHHHGS (part of SEQ ID NO: 9) N-terminally therefrom could not be foreseen as prospectively successful. Although expression in E.

*coli* of murine pCT as a poly-His fusion protein has been described in the literature (Rehli et al.), no conclusions can be drawn from this for the feasibility of human pCT expression since there is only about 77% identity at the amino acid level and therefore a completely different behavior must be expected. Furthermore, the murine pCT was not expressed directly after the putative signal peptide cleavage site (A25/V26) (Jakobs et al., 1981, Science, 213:457–459), but only a murine procalcitonin fragment shortened by 7 amino acids was expressed, which again may have unforeseeable consequences for the expressibility. Finally, the publication contains neither the exact fermentation conditions nor the achievable yields after purification of the fusion protein.

In the following specific embodiments of the invention are described in more detail:

The invention relates preferably to an isolated polypeptide comprising the amino acid sequence of human pCT, in particular if prepared using genetic engineering processes. The amino acid sequence of human pCT is shown in FIG. 1 (SEQ ID NO: 7).

The term "genetic engineering processes" in accordance with this invention also means in particular processes in which the polypeptide to be expressed is produced by eukaryotic or prokaryotic cells, the nucleic acid sequence coding for the polypeptide to be expressed and including recombinant nucleic acid sequences being introduced previously into these cells, for example by means of vectors, liposomes, projectiles or co-precipitation with salts. In another process a gene already naturally present in the cell and coding for the polypeptide to be expressed is activated by activating measures, for example by gene amplification or activation by means of artificially introduced promoter and/or enhancer sequences or deletion of repressor binding sequences such that the cell expresses the polypeptide to be expressed in larger amounts than naturally.

The term "amino acid sequence of human pCT" in accordance with this invention also means amino acid sequences slightly altered by exchange, deletion or addition of amino acids, and these alterations should have no serious negative influence on the binding properties of the polypeptide towards anti-pCT antibodies. The skilled worker can check this on the basis of appropriate binding studies using available anti-pCT antibodies.

The term "peptides" in accordance with this invention comprises amides which decompose into amino acids on hydrolysis, for example amino acid polymers such as, for example, polypeptides, oligopeptides, proteins or protein fragments. Molecules with no more than ten linked amino acids are in general called oligopeptides, with more than that they are called polypeptides.

Further polypeptides according to the invention are isolated polypeptides which contain the amino acid sequence shown in FIG. 2A or 2B and which have preferably been prepared using genetic engineering processes.

A preferred process according to is a process for the preparation of human procalcitonin wherein (i) a gene coding for a polypeptide comprising the amino acid sequence of human procalcitonin is inserted into a vector, (ii) a host organism is transformed with this gene-containing vector and (iii) the polypeptide expressed by the host organism is isolated. Preferred variants of this process according to the invention are those preparing a polypeptide having the amino acid sequence according to FIGS. 1 (SEQ ID NO: 7), 2A (SEQ ID NO: 8) or 2B (SEQ ID NO: 9).

A "vector" is in particular a DNA or RNA molecule which is capable of replication in a host organism and from which a recombinant DNA or RNA molecule can be constructed by incorporation of one or more foreign genes. Examples of common vectors are bacterial plasmids; viral genomes, in particular genomes of bacteriophages; yeast chromosomes and plasmids, in particular YEp, YIp, YRp, YAC; Ti plasmid; and vectors derived from adenoviruses, papillomaviruses and retroviruses. In order to facilitate expression of a foreign gene a vector in general has a promoter which is, if possible, physically or chemically inducible and which initiates transcription of a messenger RNA coding for the protein to be expressed. Furthermore a vector in general has a nucleic acid sequence causing a transcription stop and nucleic acid sequences causing a very efficient translation such as, for example, a ribosome binding site in the case of bacterial expression. Additionally an expression vector should have translation stop sequences in all possible reading frames.

Particularly preferred processes according to the invention comprise the vector, for example pQE-30 (SEQ ID NO: 10), coding for a fusion segment, preferably polyhistidine, which later on permits a simple purification of the procalcitonin fusion protein.

Suitable host cells for the process according to the invention are human, animal, plant or prokaryotic cells; particularly preferred are *E. coli* cells.

A "fusion protein" in accordance with this invention means a protein which comprises pCT and a further either C- or N-terminal poly- or oligopeptide which is translated in its entirety as one polypeptide. The fusion segment preferably ought to either increase the expressibility of procalcitonin and/or facilitate a later simple purification by affinity chromatography of the fusion protein.

Preferably the processes according to the invention will employ metal affinity chromatography and/or gel filtration to isolate the polypeptide according to the invention.

Metal affinity chromatography makes use of the fact that a chromatography gel matrix containing chelated doubly charged metal ions, for example $Ni^{2+}$, which still have a plurality of freely accessible coordination sites can bind reversibly to proteins containing a plurality of histidines in succession. Elution of the polyhistidine polypeptide under mild conditions may then be achieved competitively, for example by imidazole-containing buffers.

This invention further relates to a plasmid containing one or more nucleic acid sequences coding for one or more of the polypeptides according to the invention. A very particularly preferred plasmid according to the invention named internally pQE-PGT was deposited under deposition number DSM 13203 at the DSMZ Deutsche Sammlung von Mikroorganismen und Zelikulturen GmbH, Mascheroder Weg 1b, Braunschweig, Germany on Dec. 16, 1999.

Further embodiments according to the invention are animal, plant, isolated human or prokaryotic cells which can express one or more polypeptides according to the invention.

Yet another embodiment of this invention is the use of the polypeptides according to the invention as immunogens for preparing antibodies. The process according to the invention for preparing antibodies comprises the use as immunization antigen of one or more polypeptides according to the invention. Antibodies obtained by means of this process are called "antibodies according to the invention" hereinafter.

The term "antibody" in accordance with this invention means an immunoglobulin, for example an immunoglobulin of the class or subclass IgA, IgD, IgE, IgG, $IgG_{2a}$, $IgG_{2b}$, $IgG_3$, $IgG_4$, IgM. An antibody comprises at least one binding site (often called paratope) for an epitope (often also called antigenic determinant) on an antigen or hapten. Such an epitope is characterized, for example, by its three-dimensional structure and/or the presence of polar and/or apolar groups. The antibody binding site is complementary to the epitope. The antigen-antibody reaction or hapten-antibody reaction works according to the so-called "lock-and-key principle" and is in general specific to a high degree, i.e. the antibodies are capable of distinguishing small differences in primary structure, charge, three-dimensional configuration and steric arrangement of the antigen or hapten. In particular the so-called complementarity determining regions of the antibody contribute to the binding of the antibody to the antigen or hapten.

The term "antigens" comprises monovalent and polyvalent antigens. A polyvalent antigen is a molecule or a molecule complex to which more than one immunoglobulin can bind simultaneously, whereas only a single antibody can bind to a monovalent antigen at any one time. A hapten usually denotes a molecule which on its own is not immunogenic but is usually bound to a carrier for immunization purposes.

The term antibody in accordance with this invention means not only antibodies but expressly also antibody fragments such as, for example, Fab, Fv, F(ab')$_2$, Fab'; and also chimeric, humanized, bi- or oligo-specific or single-chain antibodies; furthermore also aggregates, polymers and conjugates of immunoglobulins and/or fragments thereof as long as the binding properties to the antigen or hapten are maintained. Antibody fragments can be prepared for example by enzymatic cleavage of antibodies using enzymes such as pepsin or papain. Antibody aggregates, polymers and conjugates can be generated by a multiplicity of methods, for example by heat treatment, reaction with substances such as glutaraldehyde, reaction with immunoglobulin-binding molecules, biotinylation of antibodies and subsequent reaction with streptavidin or avidin, etc.

An antibody according to this invention can be a monocloflal or a polyclonal antibody. The antibody may have been prepared according to the usual processes, for example by immunization of man or an animal such as, for example, mouse, rat, guinea pig, rabbit, horse, sheep, goat, chicken (see also Messerschmid (1996) BIOforum, 11:500–502) and subsequent preparation of the antiserum; or by establishing hybridoma cells and subsequent purification of the secreted antibodies; or by cloning and expression of nucleotide sequences or modified versions thereof coding for amino acid sequences which are responsible for binding of the natural antibody to the antigen and/or hapten.

In a preferred embodiment of the process according to the invention the polypeptides according to the invention which are used as immunization antigens may be used for the immunization in unbound and/or carrier-bound form. Typical carriers are, for example, proteins such as, for example, ovalbumin, albumin or hemocyanin, or polymers such as, for example, polyethylene glycol, polyacrylamide or poly-d-glutamine-d-lysine. The polypeptides can be bound to this carrier, for example, using carbodiimide or glutaraldehyde or else a bifunctional reagent which can also act as a spacer (for examples and coupling methods see e.g. Wong S. (1993) Chemistry of Protein Conjugation and Cross-linking, CRC Press Inc., Boca Raton).

The immunization antigen, for example, may be suspended in phosphate-buffered saline and treated with Freund's adjuvant. This emulsion may then be administered, for example, intradermally, intraperitoneally and/or subcutaneously to an animal, for example a rabbit, mouse, rat, guinea pig, horse, sheep, goat, chicken, etc. Booster injections may help to increase the immune response, it also being possible for the immunization antigen to be emulsified with incomplete Freund's adjuvant.

Polyclonal antibodies according to the invention may be obtained from the antiserum of the immunized animals. These antibodies can be further purified by means of affinity chromatography on a matrix to which, for example, pCT or pCT fragments have been bound.

In order to create monoclonal antibodies according to the invention the immune cells of immunized animals such as, for example, a mouse, are fused according to generally well-known methods (see e.g. Harlow & Lane (1988) Antibodies: A Laboratory Manual, Cold Spring Harbor Laboratory, Cold Spring Harbor; Peters et al. (1985) Monoklonale Antikörper: Herstellung und Charakterisierung, Springer Verlag) with myeloma cells to create hybridoma cells producing monoclonal antibodies (MAb), and subsequently suitable clones are isolated. The desired MAb-producing clones are selected using specific screening methods. In these the binding specificity of the antibodies released into the cell culture supernatant, for example for the immunization antigen, a possible carrier of the immunization antigen, pCT, free calcitonin, free katacalcin and free N-procalcitonin, is tested using, for example, enzyme immunoassays, radioimmunoassays and/or Western blots. Hybridomas producing the antibodies according to the invention are cloned. The hybridoma cell lines obtained in this way are then available for continuous MAb production. Larger quantities of antibodies may be obtained from, for example, cell culture supernatant, in particular from fermenters or roller cultures and from ascites.

It is advantageous depending on the desired purpose to employ only antibody fragments such as, for example, Fab, F(ab')$_2$ or Fab' fragments. These may be created, for example, by enzymatic cleavage methods known to the skilled worker (see also e.g. Harlow & Lane (1988) Antibodies: A Laboratory Manual, Cold Spring Harbor Laboratory, Cold Spring Harbor).

The antigen binding sites of an antibody are located in the so-called variable domains coded for by the V genes. Using well-known genetic engineering methods (see e.g. Sambrook et al. (1989) Molecular Cloning: A Laboratory Manual, Cold Spring Harbor Laboratory, Cold Spring Harbor, $2^{nd}$ edition; McCafferty et al. (1990) Nature 348:552–554) it is also possible to determine the corresponding nucleic acid sequence of an antibody according to the invention and thereby also the corresponding amino acid sequence, if not already known from amino acid sequencing. For analyses of this kind, the hybridoma cells or the antibody producing immune cells of immunized animals may be employed as starting material.

Knowing the nucleic acid sequence and/or amino acid sequence it is then possible using conventional genetic engineering and molecular biology methods (see also Johnson & Chiswell (1993) Current Opinion in Structural Biology, 3:564–571) to prepare humanized, chimeric, bi- or oligo-specific antibodies and peptides derived from the complementarity determining region (minimal recognition units), single-chain fragments and/or functional fusion products, for example recombinant antibody-enzyme constructs (see e.g. Larrick & Fry (1991) Human Antibodies and Hybridomas, 2:172–189; Kitano et al. (1986) Appl. Microbiol. Biotechnol., 24:282–286; Thompson et al. (1986) J. Immunol. Methods, 94:7–12) which bind to procalcitonin but not to free calcitonin, free katacalcin and free N-procalcitonin. Using such peptides included in the term "antibody" it is possible, for example, to achieve a decrease in immunogenicity and/or an enhanced efficiency when administered as a medicament or in vivo diagnostic agent and/or there will be advantages when employed as or as part of an in vitro diagnostic agent. The antibodies may also be prepared using, where appropriate, genetic engineering methods in plant cells such as, for example, yeast cells (Fischer et al. (1999) Biol. Chem., 380:825–839; Hiatt et al. (1992) Genetic Engineering, 14:49–64)), animal and prokaryotic cells (see e.g. WO 95/25172) and isolated human cells.

Furthermore, this invention also relates to animal, plant or prokaryotic cells and isolated human cells producing an antibody according to the invention.

It is also possible for the skilled worker by providing the antibodies according to the invention to identify, for example by competition experiments (see also Peters et al. (1985) Monoklonale Antikörper, Springer Verlag, chapter 12.2 "Epitop-Analyse"), other specific binding partners expressly including antibodies which bind to the epitope of an antibody according to the invention. Thus it is possible now by techniques known to the skilled worker to select specific binding partners using phage display libraries, synthetic peptide databases or recombinatorial antibody libraries (Larrick & Fry (1991) Human Antibodies and Hybridomas, 2:172–189).

A "specific binding partner" means a member of a specific binding pair. The members of a specific binding pair are two molecules each having at least one structure complementary to a structure of the other molecule, the two molecules being able to bind to each other via binding of the complementary structures. The term molecule also comprises molecule complexes such as, for example, enzymes comprising apoenzyme and coenzyme, proteins comprising a plurality of subunits, lipoproteins comprising protein and lipids, etc. Specific binding partners may be naturally occurring substances but also substances prepared by means of, for example, chemical synthesis, microbiological techniques and/or genetic engineering processes. Examples which may be mentioned to illustrate but not restrict the term specific binding partner are: thyroxine binding globulin, steroid binding proteins, antibodies, antigens, haptens, enzymes, lectins, nucleic acids, repressors, oligonucleotides and polynucleotides, protein A, protein G, avidin, streptavidin, biotin, complement component Clq, nucleic acid binding proteins, etc. Specific binding pairs are for example: antibody/antigen, antibody/hapten, operator/repressor, nuclease/nucleotide, biotin/avidin, lectin/polysaccharide, steroid/steroid binding protein, active ingredient/active ingredient receptor, hormone/hormone receptor, enzyme/substrate, IgG/protein A, complementary oligonucleotides or polynucleotides, etc.

This invention also relates to the use of the polypeptides according to the invention in affinity chromatography, in particular for purifying specific binding partners binding to pCT.

The term "affinity chromatography" means a method by which substances, in particular biopolymers, are purified and isolated and which is based on the fact that many substances can bind to their specific binding partners in a selective, noncovalent, reversible manner. The principle of the process involves the specific binding partner being bound in general covalently to an insoluble matrix (e.g. porous glasses, gels based on agarose, cellulose, dextran, polymer and silica gel) and brought into contact with a sample containing the substance. The sought-after substance is immobilized and retained by its specific interaction with the matrix-bound specific binding partner, while all other substances contained in the sample are removed by elution. The sought-after biopolymer is then detached from the matrix using a suitable eluent which cancels out the noncovalent bond between substance and specific binding partner (see also E. Buddecke (1989) Grundrisse der Biochemie, Walter de Gruyter, chapter 7 "Proteine").

This invention additionally relates to the use of the polypeptides according to the invention and/or the antibodies according to the invention as a diagnostic agent, as an ingredient of a diagnostic agent, for preparing a diagnostic agent, as a medicament, as an ingredient of a medicament and/or for preparing a medicament.

The term "diagnostic agent" means in accordance with this invention an agent serving in particular to diagnose possible diseases, establish the state of health, the physical or mental state of organisms and/or detect or quantify substances or organisms in samples. In case of a "in vitro diagnostic agent" the analyte to be detected, for example procalcitortin or anti-procalcitonin antibodies, is detected in a sample outside a living human or animal organism and/or the concentration or amount thereof is determined. The polypeptides according to the invention and/or the antibodies according to the invention may also be administered to an organism as "in vivo diagnostic agents" in unlabeled or labeled form using, for example, a radioactive isotope in the course of a function test or a scintigraphic method.

The polypeptides according to the invention may be processed further into, for example, physiologically active pCT cleavage products such as, in particular, calcitonin in order to prepare a medicament which may be used to influence calcium and bone metabolism. In addition, the polypeptides according to the invention themselves or else the antibodies according to the invention may be administered as medicaments either on their own or together with one or more pharmacologically active substances, for example for the treatment of tumors, sepsis and/or SIRS. The polypeptides according to the invention or else the antibodies according to the invention may also have their activity enhanced by modifications and/or linking to pharmacologically active substances.

This invention additionally comprises the polypeptides according to the invention and/or the antibodies according to the invention in a pharmaceutically suitable sterile injection medium. A pharmaceutically suitable sterile injection medium means, for example, a sterile pyrogen-free solution, for example saline or another electrolyte solution, such as is used conventionally in the intravenous, intramuscular, intraperitoneal or subcutaneous administration of medicaments, vaccines or contrast media.

The polypeptides according to the invention and/or the antibodies according to the invention may also be used in particular in a process for the quantitative or qualitative detection of an analyte, preferably procalcitonin or anti-procalcitonin antibodies, in a sample. In such a detection method according to the invention the polypeptides according to the invention may serve, for example, as standard antigen and/or specific binding partner in an analyte/binding partner complex.

In a quantitative test the amount or the concentration of the analyte in the sample is measured. The term "quantitative test" also comprises semi-quantitative methods which may measure only the approximate amount or concentration of the analyte in the sample or serve only to indicate relative quantities or concentrations. A qualitative test means detecting the presence of the analyte in the sample in fact or indicating that the analyte concentration in the sample is below or above a particular threshold or several particular thresholds.

The term "analyte" means the substance to be detected. Examples of analytes are listed in EP-A2-0 515 194 on pages 8–15.

A "sample" in accordance with the invention means the material presumably containing the substance to be detected. The term sample comprises, for example, biological fluids or tissue, in particular of humans and animals such as blood, plasma, serum, sputum, exudate, bronchoalveolar lavage, lymph fluid, synovial fluid, seminal fluid, vaginal mucus, feces, urine, CSF, hairs, skin, tissue samples or tissue sections. Further comprised are cell culture samples, plant fluids or tissue, forensic samples, water and waste water samples, foods, medicaments. The samples need to be pretreated where appropriate to make the analyte available for the detection method or to remove interfering sample constituents. Such a pretreatment of samples may include removal and/or lysis of cells, precipitation, hydrolysis or denaturation of sample constituents such as, for example, proteins, centrifugation of samples, treatment of the sample using organic solvents such as, for example, alcohols, in particular methanol; treatment of the sample using detergents. Often the sample is transferred into another, usually aqueous, medium which, if possible, ought not to interfere with the assay.

The detection according to the invention of an analyte with the polypeptides according to the invention and/or the antibodies according to the invention may be carried out by methods such as, for example: Western blot, dot blot, immunohistochemical test methods, immunoelectrophoresis, immunofixation electrophoresis, electroimmunodiffusion, immunoprecipitation, radial immunodiffusion, immunofixation, immunochromatography, latex agglutination, turbidimetric or nephelometric test, homogeneous or heterogeneous binding assay, one- or two-step assay, sandwich assay, indirect assay, competitive assay, point-of-care tests, etc. These and other detection methods are described, for example, in "Labor und Diagnose", ed. L. Thomas, TH-Books Verlagsgesellschaft mbH, Frankfurt, 1998, chapter 60, or in "Laboratory Techniques in Biochemistry and Molecular Biology—An Introduction to Radioimmunoassay and Related Techniques", ed. T. Chard, Elsevier, Amsterdam, 1987.

In binding assays the analyte, if present in the sample, is bound to one or more analyte-specific binding partners, and analyte/analyte-specific binding partner(s) complexes are formed.

In homogeneous binding assays free and complex-bound analytes are not separated. Examples of homogeneous immunoassays (see also Boguslaski & Li (1982) Applied Biochemistry and Biotechnology, 7:401–414) are many turbidimetric or nephelometric methods, it being possible for the specific binding partners used for the detection to be associated with latex particles; EMIT® assays; CEDIA® assays; fluorescence polarization immunoassays; luminescent oxygen channeling immunoassays (EP-A2-0 515 194; Ullman et al. (1994) Proc. Natl. Acad. Sci., 91:5426–5430; Ullman et al. (1996) Clinical Chemistry, 42:1518–1526); etc.

Heterogeneous binding assays comprise one or more separation steps and/or wash steps. The separation may be carried out by, for example, immunoprecipitation, precipitation using substances such as polyethylene glycol or ammonium sulfate, filtration, magnetic separation, binding to a solid phase such as, for example, to a test tube, a bead, a well of a microtiter plate or to filter paper or chromatography paper. In heterogeneous binding assays frequently one specific binding partner is associated with a reporter system component and one specific binding partner is associated with a solid phase (regarding indirect binding see also EP-A2-0 411 945). Here the specific binding partners may be different or the same, for example an analyte-specific monoclonal antibody may be employed both as capture agent (for example as a solid-phase antibody) and as labeled antibody if the analyte contains more than one epitope.

In heterogeneous sandwich assays the analyte is usually bound by a specific binding partner associated with a solid phase and a specific binding partner associated with a reporter system component. In the case of a sandwich immunoassay the specific binding partners may be analyte-specific antibodies or, if the analyte itself is an antibody, the antigen and/or a "modified antigen", for example a labeled antigen, antigen fragment, antigen analog. Examples of such sandwich complexes are: solid-phase antibody< >analyte< >antibody label or solid-phase antigen< >analyte (=antibody)< >antigen label.

A further embodiment of a heterogenous immunoassay is the indirect immunoassay: in this case the analyte is an antibody. One of the specific binding partners is the antigen thereof and/or a modified antigen and the other specific binding partner is an antibody binding to the analyte and/or an immunoglobulin-binding protein. Examples of such complexes which may be formed in an indirect immunoassay are: solid-phase anti-immunoglobulin antibody< >analyte (=anti-pCT antibody)< >labeled pCT or, alternatively, solid phase pCT< >analyte (=anti-pCT antibody)< >labeled protein A.

In a heterogeneous competitive immunoassay the sample analyte competes with a "modified analyte", for example a labeled analyte, analyte fragment, analyte analog, etc. for a limited number of analyte-specific binding sites. Examples illustrating the principle are: (i) sample analyte competes with an analyte associated with a reporter system component for binding to a solid-phase associated analyte-specific antibody or (ii) sample analyte competes with a solid-phase associated analyte for binding to an analyte-specific antibody associated with a reporter system component.

Sandwich assays, competitive assays and indirect assays may also be carried out as homogeneous assay methods (see also EP-A2-0 515 194).

The term "point-of-care tests" or "POC tests" has a broad meaning. It includes tests which do not need a separate analyzing or measuring device for carrying out or analyzing the test. In many cases POC tests are based on immunochromatography methods, immune complex separations by filtration and/or immunofixation techniques. POC tests are intended in particular for on-the-spot measurements, for example at the hospital bed or at home, for the emergency doctor and/or the general practitioner and not so much for the large-scale laboratory. POC tests may also be carried out in particular by persons without in-depth training in medical technology and experience in the field of laboratory medicine. The term "POC tests" in accordance with this invention also means so-called home tests or OTC (over the counter) tests which may be carried out by medical lay-persons such as, for example, the various pregnancy tests sold for home use. Further POC tests relate to, for example, the detection of heart attack markers, drugs, medicaments, infection markers and inflammation markers. In many POC tests specific binding partners are associated to filter or chromatography strips or disks during the course of the test. A positive or negative test reaction may be linked, for example, to the appearance or nonappearance of a colored band in a particular test field and/or the appearance or nonappearance of a particular symbol, for example "+", "−" and/or the intensity of the respective measured signal.

A POC test for pCT, for example, may be constructed in the following way: the sample and labeled antibodies according to the invention which are capable of binding pCT are applied to a test strip. Suitable labels are, for example, colored latex particles, colloidal gold, enzymes, etc. If pCT is present in the sample, pCT/antibody complexes will be formed. These complexes move by means of capillary force toward a section where antibodies capable of binding to different pCT epitopes are fixed, for example as a band, or will be fixed during the course of the test (for example via a biotin/avidin bridge). The labeled PCT/antibody complexes are bound in this section and form a sandwich complex with the fixed antibodies. The intensity of the label signal is proportional to the pCT sample concentration in this case. In a competitive POC test method polypeptides according to the invention may be fixed, for example, in a section of the test strip or will be fixed in the course of the test. The fixed polypeptides according to the invention would compete with pCT from the sample for binding to labeled anti-pCT antibodies. Alternatively, fixed anti-pCT antibodies and labeled polypeptides according to the invention may also be employed for constructing a competitive pCT test.

A particularly preferred embodiment of the process according to the invention is a nephelometric or turbidimetric test, in particular a test which employs antibodies according to the invention and/or polypeptides according to the invention associated to latex particles. A further preferred process is a competitive assay in which the polypeptides according to the invention are associated to a solid phase and/or a reporter system component.

This invention further relates to polypeptides according to the invention associated to a solid phase and/or a reporter system component. In addition, the antibodies according to the invention may also be associated to a solid phase and or a reporter system component.

The term "associated" has a broad meaning and comprises, for example, covalent and noncovalent binding, direct and indirect binding, adsorption to a surface and enclosure in a depression or cavity, etc. In the case of covalent binding the polypeptides according to the invention and/or antibodies according to the invention are bound to the solid phase or label via a chemical bond. Examples of noncovalent binding are surface adsorption, enclosure in cavities or binding of two specific binding partners. Apart from directly binding to the solid phase or the label, the polypeptides according to the invention and/or the antibodies according to the invention may also be bound indirectly to the solid phase or the label through specific interaction with other specific binding partners (see also EP-A2-0 411 945). This is to be illustrated in more detail with examples: the biotinylated polypeptide according to the invention may be bound to the label via label-bound avidin; or a conjugate of fluorescein and polypeptide according to the invention may be bound to the solid phase via solid-phase bound anti-fluorescein antibodies; or the antibody according to the invention may be bound to the solid phase or the label via immunoglobulin-binding proteins.

The term "solid phase" in accordance with this invention comprises an object which consists of porous and/or non porous, generally water-insoluble material and which may have very diverse shapes such as, for example, vial, test tube, microtiter plate, bead, microparticle, stick, strip, filter paper or chromatography paper, etc. In general the surface of the solid phase is hydrophilic or may be made hydrophilic.

The solid phase may comprise very diverse materials such as, for example, inorganic and/or organic materials, synthetic materials, naturally occurring materials and/or modified naturally occurring materials. Examples of solid-phase materials are polymers such as, for example, cellulose, nitrocellulose, cellulose acetate, polyvinyl chloride, polyacrylamide, cross-linked dextran molecules, agarose, polystyrene, polyethylene, polypropylene, polymethacrylate or nylon; ceramics; glass; metals, in particular noble metals such as gold and silver; magnetite; mixtures or combinations thereof; etc. The term solid phase also comprises cells, liposomes or phospholipid vesicles.

The solid phase may have a coating of one or more layers of, for example, proteins, carbohydrates, lipophilic substances, biopolymers, organic polymers or mixtures thereof in order to suppress or prevent, for example, nonspecific binding of sample constituents to the solid phase or to achieve, for example, improvements in suspension stability of particulate solid phases, shelf life, shaping stability or resistance to UV light, microbes or other destructive agents.

A "reporter system" may be one or more components, at least one component being a detectable label. A label means any molecule producing a signal by itself or capable of inducing production of a signal such as, for example, a fluorescent substance, radioactive substance, enzyme or chemiluminescent substance. The signal may be detected or measured, for example, by the enzyme activity, luminescence, light absorption, light scattering, electromagnetic or radioactive emission or a chemical reaction.

A label may be able to produce a detectable signal by itself so that no further components are necessary. Many organic molecules absorb ultraviolet and visible light, it being possible for these molecules to reach an excited energy level due to the energy transferred by light absorption and to emit the absorbed energy as light of a wavelength different from that of the incident light. Yet other labels may produce directly a detectable signal such as, for example, radioactive isotopes or dyes.

Yet other labels need additional components for signal production, that is to say the signal producing system in that case includes all components needed for generating the signal such as, for example, substrates, coenzymes, quenchers, accelerators, additional enzymes, substances reacting with enzyme products, catalysts, activators, cofactors, inhibitors, ions, etc.

Suitable labels (see also EP-A2-0 515 194; U.S. Pat. Nos. 5,340,716; 5,545,834; Bailey et al. (1987) J. Pharmaceutical & Biomedical Analysis 5:649–658) are, for example, enzymes including horseradish peroxidase, alkaline phosphatase, glucose-6-phosphate dehydrogenase, alcohol dehydrogenase, glucose oxidase, β-galactosidase, luciferase, urease and acetylcholinesterase; dyes; fluorescent substances including fluorescein isothiocyanate, rhodamine, phycoerythrin, phycocyanin, ethidium bromide, 5-dimethylaminonaphthalene-1-sulfonyl chloride and fluorescent rare earth chelates; chemiluminescent substances including luminol, isoluminol, acridine compounds, olefin, enol ether, enamine, aryl vinyl ether, dioxene, arylimidazole, lucigenin, luciferin and aequorin; sensitizers including eosin, 9,10-dibromoanthracene, methylene blue, porphyrin, phthalocyanin, chlorophyll, Rose Bengal; coenzymes; enzyme substrates; radioactive isotopes including $^{125}$I, $^{131}$I, $^{14}$C, $^{3}$H, $^{32}$P, $^{35}$S, $^{14}$C, $^{51}$Cr, $^{59}$Fe, $^{57}$Co and $^{75}$Se; particles including magnetic particles or particles, preferably latex particles, which may be labeled themselves by, for example, dyes, sensitizers, fluorescent substances, chemiluminescent substances, isotopes or other detectable labels; sol particles including gold and silver sols; liposomes or cells which may be labeled themselves by detectable labels; etc.

A reporter system may also comprise components which can interact with each other in a detectable manner at close range, for example as energy donors and energy acceptors such as, for example, photosensitizers and chemiluminescent substances (EP-A2-0 515 194), photosensitizers and fluorophores (WO 95/06877), radioactive iodine-125 and fluorophores (Udenfriend et al. (1985) Proc. Natl. Acad. Sci. 82:8672–8676), fluorophores and fluorophores (Mathis (1993) Clin. Chem. 39:1953–1959) or fluorophores and fluorescence quenchers (U.S. Pat. No. 3,996,345).

An interaction between the components includes direct energy transfer between the components, for example by light or electron radiation and via short-lived reactive chemical molecules. It further comprises processes in which the activity of one component is inhibited or enhanced by one or more others, for example inhibition of or increase in enzyme activity or inhibition of, increase or change in electromagnetic radiation emitted from the affected component (e.g. wavelength shift, polarization). The interaction between the components also comprises enzyme cascades. In this case the components are enzymes, at least one of which supplies the substrate for a second one, resulting in maximum or minimum reaction velocity of the coupled substrate conversion.

An effective interaction between the components generally takes place when these are in spatial proximity, that is, for example, within a distance of a few $\mu$m, in particular within a distance of below 600 nm, preferably below 400 nm, very particularly preferably below 200 nm.

Microparticles are commonly used as solid phase and/or label. The term "microparticle" in accordance with this invention means particles having an approximate diameter of at least 20 nm and no more than 20 $\mu$m, usually between 40 nm and 10 $\mu$m, preferably between 0.1 and 10 $\mu$m, particularly preferably between 0.1 and 5 $\mu$m, very particularly preferably between 0.15 and 2 $\mu$m. The microparticles may be shaped regularly or irregularly. They may comprise spheres, spheroids, spheres having more or less large cavities or pores. The microparticles may comprise organic material, inorganic material or a mixture or combination of both. They may comprise porous or nonporous material, swellable or non-swellable material. In principle the microparticles may have any density, however, particles having a density close to the density of water such as from about 0.7 to about 1.5 g/ml are preferred. The preferred microparticles are suspendable in aqueous solutions and stable in suspension for as long as possible. They may be transparent, partly transparent or opaque. The microparticles may comprise a plurality of layers such as, for example, the so-called core-and-shell particles having a core and one or more surrounding layers. The term microparticle comprises, for example, dye crystals, metal sols, silica particles, glass particles, magnetic particles, polymer particles, oil drops, lipid particles, dextran, and protein aggregates. Preferred microparticles are particles suspendable in aqueous solutions and comprising water-insoluble polymer material, in particular substituted polyethylenes. Very particularly preferred are latex particles made of, for example, polystyrene, acrylic acid polymers, methacrylic acid polymers, acrylonitrile polymers, acrylonitrile/butadiene/styrene, polyvinyl acetate-acrylate, polyvinylpyridine, vinyl chloride/acrylate. Of particular interest are latex particles having on their surface reactive groups such as, for example, carboxyl, amino or aldehyde groups which facilitate covalent binding, for example of specific binding partners, to the latex particles. The preparation of latex particles is described in, for example, EP 0 080 614, EP 0 227 054 and EP 0 246 446.

The invention further relates to a test kit containing one or more of the antibodies according to the invention and/or one or more of the polypeptides according to the invention. Such a kit usually contains all or only some test components in packaged form. The antibodies according to the invention and the polypeptides according to the invention may be associated to, for example, one or more solid phases and/or one or more reporter system components. The test kit may contain, for example, standards; controls; and further reagents such as, for example, buffers, washing solutions, measured signal inducing solutions and/or enzyme substrate; cuvettes; pipettes and/or instructions. A particularly preferred test kit according to the invention contains polypeptides according to the invention and/or antibodies according to the invention associated to latex particles.

A particularly preferred embodiment of the invention is the use of the polypeptides according to the invention in standards and/or controls. In detection methods the concentration, amount or activity in a sample of a substance to be detected is commonly determined using reference or standard curves. In order to obtain such reference curves, standards, also called calibrators, containing a specific known concentration, amount or activity of the analyte are measured in the detection method. In the end, the concentration, amount or activity of the analyte in the sample can be determined by comparing the measured signal values of the sample with the reference curve.

Controls contain similarly to the standards a specific known concentration, amount or activity of the analyte or a modified analyte and serve to check the detection method.

To prepare the standards and/or controls according to the invention a specific amount of one or more of the polypeptides according to the invention is added to a matrix. This matrix may be, for example a human or animal serum or plasma or even an artificial matrix such as, for example, a buffer which may contain proteins and which may also contain further substances. Standards and controls may also contain one or more additional analytes. They can be in liquid, frozen or lyophilized form and therefore may be employed in the detection methods either directly or only after preparation.

The invention further relates to stable pCT solutions which may be used, for example, as controls, standards or else for other in vitro and in vivo applications. "Stable" in this connection means that the desired property of the procalcitonin present in the solution, for example the ability to bind to specific antibodies remains generally unchanged over a specific period, in particular during liquid storage, while in "unstable" pCT solutions this property changes significantly over the same period.

Stable pCT solutions can be prepared by adding the polypeptides and sterol esters according to the invention to a serum/plasma-containing or serum/plasma-free matrix.

Particularly in pCT solutions employed as pCT controls and/or pCT standards the employed pCT may also be, for example, a peptide which has been isolated from natural sources or produced by recombination and which contains at least considerable parts of the amino acid sequence of human pCT such as, for example, relatively large pCT cleavage products. However, the peptide has to be suitable as standard and/or control serum antigen in a quantitative or qualitative pCT detection method.

The sterol esters suitable for preparing the pCT solution according to the invention belong to the steroid class of substances (gonane derivatives) which is generally characterized by an hydroxyl group in the 3 β position. The main differences are on the side chain located in the 17(20) position. The sterols constitute a large class (Beyer et al. (1981), Lehrbuch der organischen Chemie, pp 649–664 "Steroide"). Advantageously vitamin D3, estrone, stigmasterol and, particularly advantageously, cholesterol and derivatives thereof may be used.

The sterol esters to be employed according to the invention additionally and preferably have a polyethylene glycol group (PEG group) linked via a dicarboxylic acid. In principle all known dicarboxylic acids may be used; the use of succinic acid, adipic acid or sebacic acid is particularly advantageous.

In addition, the PEG group essentially ought to ensure the solubility of the sterol ester, so that the skilled worker is able to determine the optimal length easily, if necessary in an experiment. From experience the following chain lengths are advantageous: polyethylene glycol 600, polyethylene glycol 900 or polyethylene glycol 3000.

The sterol esters preferably employed for preparing the pCT solutions according to the invention are of the general formula I:

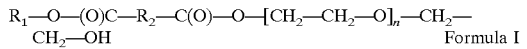

$$R_1-O-(O)C-R_2-C(O)-O-[CH_2-CH_2-O]_n-CH_2-CH_2-OH \quad \text{Formula I}$$

where n=1–200 and

R$_1$ is sterol,

R$_2$ is an aliphatic or aromatic ring of 4 to 8 carbon atoms, wherein one or more of the ring atoms is optionally replaced by N, S or O, or is a linear aliphatic carbon chain having from 0 to 12 carbon atoms, or is a branched aliphatic carbon chain having from 0 to 12 carbon atoms, wherein 0 carbon atoms represents a bond; particularly preferred is the use of sterol esters in which R$_1$ is a compound of the general formula II:

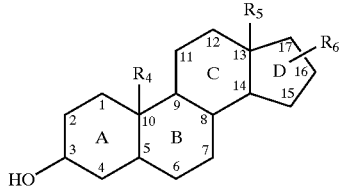

Formula II where R$_4$ and R$_5$ may be H or —CH$_3$,

R$_6$ is selected from a linear carbon chain having from 1 to 12 carbon atoms, a branched carbon chain having from 1 to 12 carbon atoms, an —OH group, and a =O group; and the rings A, B, C and D are each independently saturated, unsaturated or aromatic, and, if R$_4$ is —C(19)H$_3$, ring B may be opened between C(9) and C(10) with formation of a double bond between C(9) and C(19).

Very particularly preferred is the use of sterol esters, where the sterol residue originates from cholesterol, vitamin D3, stigmasterol or estrone. Advantageously the sterol ester is added in a concentration such that the concentration in the pCT solution is 0.05–5% by weight, preferably 0.1–3% by weight, particularly preferably 0.5–1.5% by weight.

The pCT solutions according to the invention may also contain protease inhibitors, for example aprotinin, benzamidine, bestatin, cystatin, pepstatin, PMSF, trypsin inhibitor, and/or detergents, in particular nonionic and/or zwitterionic detergents.

A particularly preferred embodiment of the pCT solution apart from the sterol esters also contains polygeline. Polygeline is a mixture of thermally degraded and cross-linked gelatin proteins and may be prepared according to DE-A 1155134 or U.S. Pat. No. 3,057,782. Advantageously polygeline is added such that the concentration in the pCT solution is 0.1–10% by weight, preferably 1–8% by weight, particularly preferably 2–6% by weight.

In order to measure the stabilizing effect—in particular in pCT solutions serving as standards and/or controls—pCT may be determined, for example, in a nephelometric measurement method.

A further embodiment of this invention comprises the use of standards, controls and pCT solutions according to the invention in methods for quantitative or qualitative detection of pCT, calcitonin, katacalcin, N-procalcitonin and/or further pCT fragments in a sample.

FIG. 1 shows the amino acid sequence of human pCT (SEQ ID NO: 7).

FIG. 2 shows the amino acid sequence of a polypeptide according to the invention without (A, SEQ ID NO: 8) and with (B, SEQ ID NO: 9) fusion segment.

FIG. 3 shows the nucleic acid sequence of vector pQE-30 (3462 base pairs), SEQ ID NO: 10.

FIG. 4 shows the nucleic acid sequence of the insert which codes for pCT (SEQ ID NO: 11) and which was cloned into pQE-30 including the cleavage sites used.

FIG. 5 shows the nucleic acid sequence of human pCT (SEQ ID NO: 12).

EXAMPLES

1. Cloning of Procalcitonin

The N terminus of pCT (see FIG. 1) was constructed by means of synthetic oligonucleotides while the construction of the C terminus was carried out by PCR (polymerase chain reaction) on the basis of genomic DNA of human placenta:

(i) N Terminus

The following two oligonucleotides were used as primers:

```
1094:                                (SEQ ID NO:1)
5' GTG GGA TCC GCA CCA TTC AGG TCT GCC CTG GAG

AGC AGC CCA GCA GAC CCG GCC ACG CTC AGT GAG GAC

GAA GCG CGC CTC CTG CTG GCT GCA CTG GTG CA 3'

1095':                               (SEQ ID NO:2)
5' GTG AAG CTT AGA TCT GGG GCT GTC CAG GCT GGA

GCC CTC TCT CTC TTG CTC CTG CTC CAG CTC ACT GGC

CTT CAT CTG CAC ATA GTC CTG CAC CAG TGC AGC CA 3'

(SEQ ID NO:3)
1098:  5' GTG GGA TCC GCA CCA TTC 3'

(SEQ ID NO:4)
1099:  5' GTG AAG CTT AGA TCT GGG GC 3'

(SEQ ID NO:5)
1100:  5' GTG TCT AGA TCT AAG CGG 3'

(SEQ ID NO:6)
1101:  5' GTG AAG CTT TTA GTT GGC 3'
``` where the respective 16 3' terminal nucleotides were complementary to each other.

The following PCR was carried out:

0.25 mM dNTP (Amersham Pharmacia, Freiburg, Germany), 1 µM each of primers 1094 and 1095, 10 mM Tris HCl, pH 8.3, 50 mM KCl, 1.5 mM MgCl$_2$, 0.001% gelatin, 2.5 U Ampli-Taq DNA polymerase (Perkin Elmer, Branchburg, N.J.) were pipetted into a 50 µl reaction mixture and were amplified by means of the Perkin Elmer thermocycler GenAmp 9700 (all further PCR reactions were carried out in the same apparatus) according to the following temperature program:
initial: 94° C. 5 min,
5×cycle: 94° C. 30 s, 52° C. 30 s and 72° C. 30 s,
terminal: 72° C. 10 min.

5 µl of this mixture were transferred into a fresh 50 µl mixture as above but using the primers 1098 and 1099 and the reaction was carried out using the following temperature program:
initial: 94° C. 5 min,
30×cycle: 94° C. 30 s, 56° C. 30 s and 72° C. 30 s,
terminal: 72° C. 10 min.

5 µl of this mixture were ligated with 0.5 µg of vector pCR2.1 from the Invitrogen TA cloning kit in accordance with the manufacturer's instructions and transformed into *E.coli* INVαF'. The newly constructed plasmid was isolated and sequenced using standard methods and, during the course of this, an L to R amino acid exchange at position 37 of procalcitonin was found.

(ii) C Terminus

Genomic DNA was isolated from 2 g of human placental tissue using standard methods (all protocols described as standard methods are from "Current Protocols in Molecular Biology", 1995, Wiley & Sons Inc., New York, USA) and employed as template for the following PCR:

0.5 µg (1 µl) of human genomic DNA as template and 1 µg each of primers 1100 and 1101 were pipetted into a 50 µl reaction mixture according to the manufacturer's instructions for the Taq PCR core kit, cat. No: 201223 (Qiagen, Hilden, Germany) and amplified according to the following temperature program:
initial: 94° C. 3 min,
30×cycle: 94° C. 30 s, 45° C. 30 s and 72° C. 30 s,
terminal: 72° C. 10 min.

5 µl of this mixture were ligated with 0.5 µg of vector pCR2.1 from the Invitrogen TA cloning kit in accordance with the manufacturer's instructions and transformed into *E.coli* INVαF'. The novel plasmid was isolated and sequenced using standard methods, confirming the presence of the wild-type sequence.

(iii) Construction of the Expression Plasmid

1 µg of vector pQE-30 (Qiagen) was linearized using restriction endonucleases BamHI and HindIII (all restriction endonucleases were purchased from Boehringer Mannheim, Mannheim, Germany). In addition, the N terminus coding region was excised from the plasmid pCR2.1 containing the N terminus coding region using BamHI and HindIII (BamHI and HindIII had been artificially introduced by the PCR), isolated using standard methods and ligated into the linearized pQE-30 vector. The construct was isolated and linearized using BglII and HindIII (BglII is naturally present at the 3' end of the N terminus and could be employed here for the construction). Finally, the C terminus was excised from the vector pCR2.1 containing the C terminus using BglII and HindIII, isolated using standard methods and ligated into the pQE-30 vector linearized by BglII and HindIII and already containing the N terminus coding region. The clone containing the correct plasmid was identified and the construct was verified by sequencing. The insert used for the construction and extending from BamHI to HindIII is shown in FIG. 4; the natural human pCT sequence is shown in FIG. 5.

2. Expression of Procalcitonin

The expression of procalcitonin was first carried out on the small scale of 1 ml:

1 ml of LB medium (Current Protocols in Molecular Biology) containing 50 µg of ampicillin (Sigma, Deisenhofen, Germany) was inoculated with a single colony of *E. coli* strain JM109 harboring the expression plasmid and induced at an OD$_{600}$ of 0.4 with 1 mM IPTG (isopropyl thiogalactoside, Sigma) for 2 h. Unexpectedly, strong expression of the fusion protein of human pCT and the N-terminal segment MRGSHHHHHHGS of the pQE vector was found when the total protein of the culture was analyzed in a Coomassie-stained PAGE gel (Current Protocols in Molecular Biology).

Thereafter, expression was carried out on a larger scale using standard conditions, i.e. an overnight culture of a single clone was set up in 100 ml of LB medium containing 50 µg/ml ampicillin and shaken at 37° C. This culture was grown until stationary and then diluted 1:50 in 1 l of fresh LB medium (ampicillin 50 µg/ml), further shaken at 37° C. and induced at an OD$_{600}$ of 0.6 with 1 mM IPTG for 3 h.

Surprisingly, a drastic decline or a complete stop of fusion protein expression was detected in this case. This negative result was reproducible, leading to the conclusion that the fusion protein is toxic for *E. coli* and there is very rapid selection of mutants which do not express the fusion protein or express it only very poorly. Therefore an attempt was made to optimize the expression.

In this context the strain used for expression was varied (JM109, M15, BL21 and W3110 (Stratagene, La Jolla, Calif.)), the selection pressure level was varied by changing the ampicillin concentration, the strength of induction was varied by changing the IPTG concentration and the expression time was varied by monitoring the strength of induction time course after induction.

The following optimal parameters were found thereby:

JM109 cells freshly transformed with the expression plasmid were grown with shaking overnight in LB medium with 100 µg/ml ampicillin at 37° C. and then diluted 1:50 in 1 l of fresh LB medium (ampicillin 100 µg/ml) and further shaken at 37° C. and induced at an OD$_{600}$ of 0.4 with 2 mM IPTG for 3 h.

By following these optimized conditions about 13 mg of fusion protein were reproducibly obtained from a 1 l culture after purification under native conditions by metal affinity chromatography according to the manufacturer's instructions (Talon Metal Affinity Resin, Clontech, Palo Alto, Calif.) and subsequent gel filtration on Superdex™75 HiLoad (Amersham Pharmacia).

3. Amino Terminal Sequencing

The amino terminal sequence of recombinant human procalcitonin was determined by automatic Edman degradation in an Applied Biosystems 477A sequencer.

The amino terminal sequence found is identical after that encoded by the pQE vector sequence to that found for pCT from a human thyroid tumor (J. M. Conlon et al. (1988) Biochem. J. 256:245–250) (see Table 1). J. 256:245–250) (see Table 1).

TABLE 1

Amino terminal sequence of human pCT and recombinant human pCT

| Protein | Amino acid sequence | Reference |
|---|---|---|
| Human pCT (thyroid tumor) | A-P-F-R-S-A-L-E-S-S-P | Conlon et al. (1988) |
| Rec. human pCT | <u>M-R-G-S-H-H-H-H-H-H-G-S</u>-A-P-F-R-S-A-L-E-S-S-P * | This invention |

*pQE vector fusion segment (underlined)

4. Relative Molecular Mass Determination by Mass Spectrometry

The determination of the relative molecular mass of the prepared recombinant procalcitonin was carried out by means of electrospray mass spectrometry. Recombinant pCT obtained after expression and purification was dialyzed against distilled water and measured at a concentration of 50 µg/ml in methanol/water/acetic acid (50/50/0.1) (orifice voltage 90 V; ion spray voltage 5000 V).

The mean molecular mass of recombinant human pCT calculated from the obtained spectrum is 14,235±2 dalton. The result corresponds very well with the theoretical mass of 14,239 dalton calculated on the basis of the theoretical amino acid sequence (J. M. Conlon et al. (1988) Biochem. J., 256:245–250) and taking into account the pQE vector fusion segment (pQE vector: MRGSHHHHHHGS) and the amino acid exchange at position 37 (L to R) and therefore confirms the expression of recombinant human pCT.

5. Determination of Reactivity in a LUMItest® PCT

The LUMItest® PCT (B.R.A.H.M.S, Berlin, Germany) is an immunoluminometric assay for determining procalcitonin. Two monoclonal antibodies binding to procalcitonin at two different sites (calcitonin and katacalcin segments) are employed here.

After performing the assay according to the manufacturer's description, the luminescence signals are determined in a suitable luminometer. The size of the luminescence signal is directly proportional to the pCT concentration of the respective sample. From the luminescence signal values for the accompanying standards a standard curve can be constructed, from which the unknown procalcitonin sample concentration may be read off.

Recombinant pCT obtained after expression and purification was determined in two different dilutions in a LUMItest® PCT according to the manufacturer's instructions (see Table 2).

TABLE 2

Measured values determined in a BeriLux® Analyzer 250 (RLU = relative light units)

| Sample | RLU | ng pCT/ml |
|---|---|---|
| Standard S1 | 72 | 0.08 |
| Standard S2 | 169 | 0.49 |
| Standard S3 | 467 | 1.94 |
| Standard S4 | 6643 | 20.5 |
| Standard S5 | 97085 | 212 |
| Standard S6 | 215415 | 527 |
| Rec. pCT dil. 1 | 18742 | 50.41 |
| Rec. pCT dil. 2 | 1056 | 4.46 |

The following pCT content according to LUMItest® PCT is calculated for the two samples examined, taking into account the two dilutions employed (1:10,000 and 1:100,000).

Rec. pCT dil. 1: 0.5041 mg/ml
Rec. pCT dil. 2: 0.4463 mg/ml

This investigation provides support for the identity of recombinant pCT and human pCT and shows the usability of rec. pCT, for example as standard and/or control serum material in a diagnostic assay for determining human pCT.

6. Preparation of Monoclonal Antibodies Against Recombinant pCT (i) Immunization of Mice BALB/c mice were immunized intraperitoneally with 20 µg of rec. pCT in complete Freund's adjuvant. A booster of 20 µg of rec. pCT in incomplete Freund's adjuvant (ICN Biomedical GmbH, Eschwege, Germany) followed after 4 weeks and another booster of 20 µg of rec. pCT without Freund's adjuvant after 8 weeks. On the last three days before fusion the mice were boosted intravenously each day by 20 µg of recombinant pCT.

(ii) Fusion

After killing the mice by $CO_2$ inhalation the spleens were removed and single cell suspensions were prepared in serum-free Dulbecco's modified Eagle medium (DMEM, CC Pro GmbH, Neustadt/W, Germany). The cells were centrifuged (652×g) and washed twice in DMEM. Subsequently the cell number was determined by means of trypan blue staining. $2 \times 10^7$ myeloma cells (Sp2/0) were added to about $10^8$ spleen cells. After centrifugation (360×g) the supernatant was discarded, 1 ml of polyethylene glycol solution (PEG 4000, Merck Eurolab, Bruchsal, Germany; ca. 50% in DMEM) was added to the cell pellet, and the resuspended cells were incubated for 1 minute at 37° C. About 10 ml of DMEM were subsequently added dropwise and incubated at room temperature for 2 to 4 minutes. The fused cells were spun down (326×g) and the pellet was resuspended in DMEM+20% FBS (fetal bovine serum, BioWhittaker Europe, Verviers, Belgium)+HAT solution (CC Pro GmbH, Neustadt/W, Germany) and introduced into 24-well cell culture dishes (Costar). The approximate cell concentration per well was $5 \times 10^4$ to $5 \times 10^6$.

2–3 weeks later the resulting cell colonies (hybrids) were removed and transferred into new culture dishes.

(iii) Specificity Assay

The specificity of the antibodies released into the cell culture was tested in a first step using microtiter plates coated with immunization antigen (Nunc, type B), coating 0.2 µg/ml≈0.003 µg/well.

100 µl of cell culture supernatant (dilution 1:2) were pipetted into each well of the microtiter plate and incubated at +15 to +25° C. for 1 hour. After washing the plate twice using washing solution POD (OSEW; Dade Behring, Marburg, Germany) 100 µl of anti-mouse IgG/F(ab')$_2$-POD conjugate (Dade Behring, Marburg, Germany) were introduced into each well and incubated at +15 to +25° C. for 1 hour. After washing the plate twice again 100 μl of Chromogen TMB solution (Dade Behring, Marburg, Germany) were introduced into each well and incubated at +15 to +25° C. for a further 30 minutes. After the incubation, 100 μl of stop solution POD (Dade Behring, Marburg, Germany) were introduced into each well and the microtiter plate was analyzed at 450 nm in a BEP II (Behring ELISA Processor II).

In a 2nd step the hybrids were tested as described above using microtiter plates (Nunc, type B) coated with the following peptides:

i. Recombinant human pCT (0.03 μg/well)
ii. Calcitonin human BSA conjugate (0.5 μg/well, Bachem, prod. No.: H-2250)
iii. Katacalcin human (PDN-21) BSA conjugate (0.5 μg/well, Peninsula, prod. No. 6004)
iv. Calcitonin N-terminal flanking peptide BSA conjugate (0.5 μg/well, Bachem, prod. No.: H-3076)=human N-procalcitonin The results are listed in Table 3.

TABLE 3

Determination of antibody specificity by analyzing the microtiter plates at 450 nm in a BEP II (Behring ELISA Processor II).

| | Extinction at 450 nm | | | |
|---|---|---|---|---|
| Hybrid/(clone) | Recombinant human procalcitonin | Calcitonin | Katacalcin | N-procalcitonin |
| 99-41/14 (032) | 2.5 | 0.834 | 0.068 | 0.025 |
| 99-41/5 (05) | 2.5 | 0.010 | 2.5 | 0.014 |
| 99-246/58 | 2.5 | 0.032 | 0.030 | 2.246 |

(iv) Cloning

Single hybrid cells producing the antibodies according to the invention (binding to human pCT) were cloned using a micromanipulator (Leitz, Wetzlar, Germany).

(v) Antibody Subclass Determination

The antibody subclass is determined by means of the IsoStrip™-Mouse Monoclonal Antibody Isotyping Kit from Boehringer Mannheim, Germany.

(vi) Antibody Production

For the production of larger quantities of the antibodies according to the invention the corresponding cell clones are transferred to roller bottles (Corning Costar Deutschland, Bodenheim) and expanded to the desired final volume at +37° C. Afterward, the roller culture suspension is filtered through 0.22 μm to remove the cells. The now cell-free antibody solution is concentrated via ultrafilters (30 kilodalton cutoff) and subsequently purified.

(vii) Antibody Purification

The antibody solution obtained is pH-adjusted with 0.14 M phosphate buffer pH 8.6 and applied to a chromatography column packed with rProtein A Sepharose Fast Flow (Amersham Pharmacia) (1 ml of rProtein A Sepharose Fast Flow is employed per 10 mg of antibody to be purified). All unbound components are removed by washing the column in 0.14 M phosphate buffer pH 8.6. The bound antibody is eluted from the column by 0.1 M citric acid pH 3.0 and dialyzed against 0.05 M sodium acetate+0.5 M NaCl+0.05 M tris+0.01% sodium azide pH 7.0.

7. Detection of pCT in a Sample (i) MAb Binding to Latex Particles

One each of a monoclonal anti-calcitonin antibody according to the invention and of a monoclonal anti-katacalcin antibody according to the invention was bound to latex particles prepared according to EP-0246 446 and having a diameter of from 250 to 310 nm:

The latex polymer used was diluted to a solids content of 4% by weight using distilled water. The antibodies to be bound were diluted to a protein content of 5 mg/ml using 0.05 M sodium acetate+0.5 M NaCl+0.05 M tris+0.01% sodium azide pH 7.0. 1 ml of the abovementioned polymer was mixed with 200 μl of antibody solution. Then 0.050 ml of a 20% Tween 20 solution (Merck Eurolab, Darmstadt, Germany) was added and the mixture was mixed again. 0.025 ml of 1 N HCl was added thereto resulting in a pH of about 3. After incubation at room temperature for 30 minutes, 0.25 ml of 1 M phosphate buffer pH 6.5 and 0.25 ml of sodium cyanoborohydride (25 mg/ml) were added and mixed well. This was followed by incubation at room temperature for one hour.

This loading mixture was then centrifuged at about 50,000 g for 30 minutes. The supernatant was discarded. The residue was resuspended in 4 ml of imidazole buffer pH 8.1 (5 g/l imidazole, 40 g/l sucrose, 1 g/l human albumin). This was followed by sonication (Branson Sonifier B15) for 30 seconds. The reagent redispersed in this way was diluted in a volume ratio of 1:7.5 using the imidazole buffer mentioned before and sonicated again for 30 seconds.

(ii) Preparation of a Standard/Control

The protein content of recombinant pCT obtained after expression and purification was determined in the preparation by means of a protein determination according to Lowry et al. (1951, J. Biol. Chem. 193, 265–275). In order to prepare a standard, a suitable amount of this preparation was taken up in phosphate-buffered saline with 10 g/l bovine serum albumin, and the recombinant pCT content was calculated.

(iii) Detection of pCT

The reagents prepared according to Example 7(i) by binding of the anti-calcitonin antibody according to the invention and the anti-katacalcin antibody according to the invention to latex particles were mixed in a volume ratio of 1+1 and employed for measuring pCT in a standard and in the sera of patients in a Behring Nephelometer Analyser (BNA, Dade Behring, Marburg, Germany). The mixed reagent is agglutinated when mixed with pCT-containing samples. The intensity of the scattered light in the BNA is dependent on the sample pCT concentration, so that the pCT concentration in the sample can be determined by comparison with dilutions of a standard of known concentration. The Behring Nephelometer Analyser automatically makes the necessary standard dilutions using N-Diluens (Dade Behring, Marburg, Germany). The measured result was automatically calculated using a logit-log function. For the measurement 100 μl of sample or standard are mixed with 100 μl of N-Diluens (Dade Behring, Marburg, Germany) and 40 μl of the mixed reagent in a reaction cuvette and the change in the measured signal (in bit) was measured in the BNA after 12 minutes. The results are summarized in Table 4.

TABLE 4

Standard curve and measurement of samples

| Sample | Measured signal BNA in bit | ng pCT/ml |
|---|---|---|
| Standard dilution 1 | 2727 | 250* |
| Standard dilution 2 | 1972 | 125* |
| Standard dilution 3 | 1152 | 62.5* |
| Standard dilution 4 | 450 | 31.3* |

TABLE 4-continued

Standard curve and measurement of samples

| Sample | Measured signal BNA in bit | ng pCT/ml |
|---|---|---|
| Standard dilution 5 | 157 | 15.6* |
| Standard dilution 6 | 54 | 7.8* |
| Standard dilution 7 | 26 | 3.9* |
| Standard dilution 8 | 14 | 2.0* |
| Normal serum | −188 | <2.0 |
| pCT-containing serum 1 | 219 | 19.3 |
| pCT-containing serum 2 | 770 | 46.3 |
| pCT-containing serum 3 | 1594 | 90.7 |
| pCT-containing serum 4 | 627 | 39.6 |
| pCT-containing serum 5 | 43 | 6.3 |

*calculated on the basis of the standard employed

8. Preparation of a Stable pCT Solution (i) Preparation of the pCT Solution

In order to prepare the pCT solution particularly suitable as standard and/or control, a suitable amount of recombinant pCT obtained after expression and purification was taken up in different matrices.

Matrix 1:

Phosphate-buffered saline pH 7.2+1 g/l $NaN_3$+40 g/l Polygeline (Hoechst Marion Roussel Deutschland GmbH, prod. No. 125590)+80,000 kIU/l Antagosan® (active ingredient: aprotinin, Hoechst Marion Roussel Deutschland GmbH, prod. No. 122162)

Matrix 2:

Phosphate-buffered saline pH 7.2+1 g/l $NaN_3$+40 g/l Polygeline (Hoechst Marion Roussel Deutschland GmbH, prod. No. 125590)+80,000 kIU/l Antagosan® (active ingredient: aprotinin, Hoechst Marion Roussel Deutschland GmbH, prod. No. 122162)+10 g/l cholesterol, water-soluble (Sigma, order No.: C-1145)

Matrix 3:

Lipoprotein-free human citrate plasma (prepared according to Example 4 of EP-0 606 616)+1 g/l $NaN_3$+80,000 kIU/l Antagosan® (active ingredient: aprotinin, Hoechst Marion Roussel Deutschland GmbH, prod. No. 122162)

Matrix 4:

Lipoprotein-free human citrate plasma (prepared according to Example 4 of EP-0 606 616)+1 g/l $NaN_3$+80,000 kIU/l Antagosan® (active ingredient: aprotinin, Hoechst Marion Roussel Deutschland GmbH, prod. No. 122162)+10 g/l cholesterol, water-soluble (Sigma, order No.: C-1145)

(ii) Stability Test

In order to test its stability, the pCT solution was stored at +2° C. to +8° C. and, after different storage periods, the change in the measured signal (in bit) of the pCT detection method according to Example 7(iii) was determined. The results are summarized in Table 5.

TABLE 5

Shelf life of pCT solutions pCT solution (125 ng/ml)

|  | Measured signal BNA in bit after preparation | Measured signal BNA in bit after 3 weeks of storage at +2° C.–+8° C. | Deviation in % from measured signal BNA after preparation | Measured signal BNA in bit after 8 weeks of storage at +2° C.–+8° C. | Deviation in % from measured signal BNA after preparation |
|---|---|---|---|---|---|
| Matrix 1 | 1629 | 489 | −70 | — | — |
| Matrix 2 | 1916 | 1959 | 2.2 | 1821 | −5.0 |
| Matrix 3 | 1840 | 1321 | −28.2 | — | — |
| Matrix 4 | 1757 | 1324 | −24.6 | — | — |

Result: The pCT solution based on matrix 2 is particularly stable. The addition of cholesterol also promotes the stability of pCT in serum/plasma matrix.

What is claimed is:

1. An isolated recombinant polypeptide comprising an amino acid sequence SEQ ID NO: 8.

2. An isolated recombinant polypeptide comprising an amino acid sequence SEQ ID NO: 9.

3. A composition comprising the polypeptide according to claim 1 and a pharmaceutically-acceptable, sterile injection medium.

4. A composition comprising the polypeptide according to claim 2 and a pharmaceutically-acceptable, sterile injection medium.

5. A diagnostic agent comprising the polypeptide according to claim 1.

6. A diagnostic agent comprising the polypeptide according to claim 2.

7. A composition comprising the polypeptide according to claim 1 and a pharmaceutically-acceptable carrier.

8. A composition comprising the polypeptide according to claim 2 and a pharmaceutically-acceptable carrier.

9. A method for preparing antibodies to the polypeptide according to claim 1 comprising immunizing a host with said polypeptide.

10. A method for preparing antibodies to the polypeptide according to claim 2 comprising immunizing a host with said polypeptide.

11. A standard and/or a control composition comprising the polypeptide according to claim 1.

12. A standard and/or a control composition comprising the polypeptide according to claim 2.

13. A test kit comprising the polypeptide according to claim 1.

14. A test kit comprising the polypeptide according to claim 2.

15. A solution comprising the polypeptide according to claim 1, wherein said polypeptide is stable during liquid storage.

16. A solution comprising the polypeptide according to claim 2, wherein said polypeptide is stable during liquid storage.

* * * * *

UNITED STATES PATENT AND TRADEMARK OFFICE
CERTIFICATE OF CORRECTION

PATENT NO. : 6,905,687 B2
DATED : June 14, 2005
INVENTOR(S) : Harald Althaus and Hans-Peter Hauser It is certified that error appears in the above-identified patent and that said Letters Patent is hereby corrected as shown below:

Title page,
Item [62], Related U.S. Application Data, "Dec. 22, 2001," should read -- Dec. 22, 2000, --.

Signed and Sealed this

Twenty-fourth Day of January, 2006

JON W. DUDAS
*Director of the United States Patent and Trademark Office*

SEQUENCE LISTING

<160> NUMBER OF SEQ ID NOS: 12

<210> SEQ ID NO 1
<211> LENGTH: 101
<212> TYPE: DNA
<213> ORGANISM: Unknown Organism
<220> FEATURE:
<223> OTHER INFORMATION: Description of Unknown Organism: Primer, non
      genomic DNA

<400> SEQUENCE: 1
gtgggatccg caccattcag gtctgccctg gagagcagcc cagcagaccc ggccacgctc       60
agtgaggacg aagcgcgcct cctgctggct gcactggtgc a                          101

<210> SEQ ID NO 2
<211> LENGTH: 104
<212> TYPE: DNA
<213> ORGANISM: Unknown Organism
<220> FEATURE:
<223> OTHER INFORMATION: Description of Unknown Organism: Primer, non
      genomic DNA -continued

<400> SEQUENCE: 2

```
gtgaagctta gatctggggc tgtccaggct ggagccctct ctctcttgct cctgctccag     60
ctcactggcc ttcatctgca catagtcctg caccagtgca gcca                    104
```

<210> SEQ ID NO 3
<211> LENGTH: 18
<212> TYPE: DNA
<213> ORGANISM: Unknown Organism
<220> FEATURE:
<223> OTHER INFORMATION: Description of Unknown Organism: Primer, non
      genomic DNA

<400> SEQUENCE: 3

```
gtgggatccg caccattc                                                  18
```

<210> SEQ ID NO 4
<211> LENGTH: 20
<212> TYPE: DNA
<213> ORGANISM: Unknown Organism
<220> FEATURE:
<223> OTHER INFORMATION: Description of Unknown Organism: Primer, non
      genomic DNA

<400> SEQUENCE: 4

```
gtgaagctta gatctggggc                                                20
```

<210> SEQ ID NO 5
<211> LENGTH: 18
<212> TYPE: DNA
<213> ORGANISM: Unknown Organism
<220> FEATURE:
<223> OTHER INFORMATION: Description of Unknown Organism: Primer, non
      genomic DNA

<400> SEQUENCE: 5

```
gtgtctagat ctaagcgg                                                  18
```

<210> SEQ ID NO 6
<211> LENGTH: 18
<212> TYPE: DNA
<213> ORGANISM: Unknown Organism
<220> FEATURE:
<223> OTHER INFORMATION: Description of Unknown Organism: Primer, non
      genomic DNA

<400> SEQUENCE: 6

```
gtgaagcttt tagttggc                                                  18
```

<210> SEQ ID NO 7
<211> LENGTH: 116
<212> TYPE: PRT
<213> ORGANISM: Unknown Organism
<220> FEATURE:
<223> OTHER INFORMATION: Description of Unknown Organism: Protein, human
      procalcitonin

<400> SEQUENCE: 7

```
Ala Pro Phe Arg Ser Ala Leu Glu Ser Ser Pro Ala Asp Pro Ala Thr
  1               5                  10                  15

Leu Ser Glu Asp Glu Ala Arg Leu Leu Leu Ala Ala Leu Val Gln Asp
             20                  25                  30

Tyr Val Gln Met Lys Ala Ser Glu Leu Glu Gln Glu Gln Glu Arg Glu
         35                  40                  45
```

```
Gly Ser Ser Leu Asp Ser Pro Arg Ser Lys Arg Cys Gly Asn Leu Ser
        50                  55                  60

Thr Cys Met Leu Gly Thr Tyr Thr Gln Asp Phe Asn Lys Phe His Thr
 65                  70                  75                  80

Phe Pro Gln Thr Ala Ile Gly Val Gly Ala Pro Gly Lys Lys Arg Asp
                85                  90                  95

Met Ser Ser Asp Leu Glu Arg Asp His Arg Pro His Val Ser Met Pro
            100                 105                 110

Gln Asn Ala Asn
        115

<210> SEQ ID NO 8
<211> LENGTH: 116
<212> TYPE: PRT
<213> ORGANISM: Unknown Organism
<220> FEATURE:
<223> OTHER INFORMATION: Description of Unknown Organism: Protein, human
      procalcitonin

<400> SEQUENCE: 8

Ala Pro Phe Arg Ser Ala Leu Glu Ser Ser Pro Ala Asp Pro Ala Thr
 1               5                  10                  15

Leu Ser Glu Asp Glu Ala Arg Leu Arg Leu Ala Ala Leu Val Gln Asp
            20                  25                  30

Tyr Val Gln Met Lys Ala Ser Glu Leu Glu Gln Glu Gln Glu Arg Glu
        35                  40                  45

Gly Ser Ser Leu Asp Ser Pro Arg Ser Lys Arg Cys Gly Asn Leu Ser
    50                  55                  60

Thr Cys Met Leu Gly Thr Tyr Thr Gln Asp Phe Asn Lys Phe His Thr
 65                  70                  75                  80

Phe Pro Gln Thr Ala Ile Gly Val Gly Ala Pro Gly Lys Lys Arg Asp
                85                  90                  95

Met Ser Ser Asp Leu Glu Arg Asp His Arg Pro His Val Ser Met Pro
            100                 105                 110

Gln Asn Ala Asn
        115

<210> SEQ ID NO 9
<211> LENGTH: 128
<212> TYPE: PRT
<213> ORGANISM: Unknown Organism
<220> FEATURE:
<223> OTHER INFORMATION: Description of Unknown Organism: Protein, human
      procalcitonin

<400> SEQUENCE: 9

Met Arg Gly Ser His His His His His His Gly Ser Ala Pro Phe Arg
 1               5                  10                  15

Ser Ala Leu Glu Ser Ser Pro Ala Asp Pro Ala Thr Leu Ser Glu Asp
            20                  25                  30

Glu Ala Arg Leu Arg Leu Ala Ala Leu Val Gln Asp Tyr Val Gln Met
        35                  40                  45

Lys Ala Ser Glu Leu Glu Gln Glu Gln Glu Arg Glu Gly Ser Ser Leu
    50                  55                  60

Asp Ser Pro Arg Ser Lys Arg Cys Gly Asn Leu Ser Thr Cys Met Leu
 65                  70                  75                  80

Gly Thr Tyr Thr Gln Asp Phe Asn Lys Phe His Thr Phe Pro Gln Thr
                85                  90                  95
```

```
Ala Ile Gly Val Gly Ala Pro Gly Lys Lys Arg Asp Met Ser Ser Asp
        100                 105                 110

Leu Glu Arg Asp His Arg Pro His Val Ser Met Pro Gln Asn Ala Asn
        115                 120                 125

<210> SEQ ID NO 10
<211> LENGTH: 3462
<212> TYPE: DNA
<213> ORGANISM: Unknown Organism
<220> FEATURE:
<223> OTHER INFORMATION: Description of Unknown Organism: Vectorsequence
      , DNA

<400> SEQUENCE: 10
ctcgagaaat cataaaaaat ttatttgctt tgtgagcgga taacaattat aatagattca      60
attgtgagcg gataacaatt tcacacagaa ttcattaaag aggagaaatt aactatgaga     120
ggatcgcatc accatcacca tcacggatcc gcatgcgagc tcggtacccc gggtcgacct     180
gcagccaagc ttaattagct gagcttggac tcctgttgat agatccagta atgacctcag     240
aactccatct ggatttgttc agaacgctcg gttgccgccg gcgttttttt attggtgaga     300
atccaagcta gcttggcgag attttcagga gctaaggaag ctaaaatgga gaaaaaaatc     360
actggatata ccaccgttga tatatcccaa tggcatcgta agaacatttt tgaggcattt     420
cagtcagttg ctcaatgtac ctataaccag accgttcagc tggatattac ggcctttttt     480
aagaccgtaa agaaaaataa gcacaagttt tatccggcct ttattcacat tcttgcccgc     540
ctgatgaatg ctcatccgga atttcgtatg gcaatgaaag acggtgagct ggtgatatgg     600
gatagtgttc acccttgtta caccgttttc catgagcaaa ctgaaacgtt ttcatcgctc     660
tggagtgaat accacgacga tttccggcag tttctacaca tatattcgca agatgtggcg     720
tgttacggtg aaaacctggc ctatttccct aaagggttta ttgagaatat gttttttcgtc     780 tcagccaatc cctgggtgag tttcaccagt tttgatttaa acgtggccaa tatggacaac     840
ttcttcgccc ccgttttcac catgggcaaa tattatacgc aaggcgacaa ggtgctgatg     900
ccgctggcga ttcaggttca tcatgccgtc tgtgatggct tccatgtcgg cagaatgctt     960
aatgaattac aacagtactg cgatgagtgg cagggcgggg cgtaattttt ttaaggcagt    1020
tattggtgcc cttaaacgcc tggggtaatg actctctagc ttgaggcatc aaataaaacg    1080
aaaggctcag tcgaaagact gggcctttcg ttttatctgt tgtttgtcgg tgaacgctct    1140
cctgagtagg acaaatccgc cgctctagag ctgcctcgcg cgtttcggtg atgacggtga    1200
aaacctctga cacatgcagc tcccggagac ggtcacagct tgtctgtaag cggatgccgg    1260
gagcagacaa gcccgtcagg gcgcgtcagc gggtgttggc gggtgtcggg gcgcagccat    1320
gacccagtca cgtagcgata gcggagtgta tactggctta actatgcggc atcagagcag    1380
attgtactga gagtgcacca tatgcggtgt gaaataccgc acagatgcgt aaggagaaaa    1440
taccgcatca ggcgctcttc cgcttcctcg ctcactgact cgctgcgctc ggtctgtcgg    1500
ctgcggcgag cggtatcagc tcactcaaag gcggtaatac ggttatccac agaatcaggg    1560
gataacgcag gaaagaacat gtgagcaaaa ggccagcaaa aggccaggaa ccgtaaaaag    1620
gccgcgttgc tggcgttttt ccataggctc cgcccccctg acgagcatca caaaaatcga    1680
cgctcaagtc agaggtggcg aaacccgaca ggactataaa gataccaggc gtttccccct    1740
ggaagctccc tcgtgcgctc tcctgttccg accctgccgc ttaccggata cctgtccgcc    1800
tttctccctt cgggaagcgt ggcgctttct caatgctcac gctgtaggta tctcagttcg    1860
```

-continued

```
gtgtaggtcg ttcgctccaa gctgggctgt gtgcacgaac cccccgttca gcccgaccgc    1920
tgcgccttat ccggtaacta tcgtcttgag tccaacccgg taagacacga cttatcgcca    1980
ctggcagcag ccactggtaa caggattagc agagcgaggt atgtaggcgg tgctacagag    2040
ttcttgaagt ggtggcctaa ctacggctac actagaagga cagtatttgg tatctgcgct    2100
ctgctgaagc cagttacctt cggaaaaaga gttggtagct cttgatccgg caaacaaacc    2160
accgctggta gcggtggttt ttttgtttgc aagcagcaga ttacgcgcag aaaaaaagga    2220
tctcaagaag atcctttgat cttttctacg gggtctgacg ctcagtggaa cgaaaactca    2280
cgttaaggga ttttggtcat gagattatca aaaggatct tcacctagat ccttttaaat     2340
taaaaatgaa gttttaaatc aatctaaagt atatatgagt aaacttggtc tgacagttac    2400
caatgcttaa tcagtgaggc acctatctca gcgatctgtc tatttcgttc atccatagct    2460
gcctgactcc ccgtcgtgta gataactacg atacgggagg gcttaccatc tggccccagt    2520
gctgcaatga taccgcgaga cccacgctca ccggctccag atttatcagc aataaaccag    2580
ccagccggaa gggccgagcg cagaagtggt cctgcaactt tatccgcctc catccagtct    2640
attaattgtt gccgggaagc tagagtaagt agttcgccag ttaatagttt gcgcaacgtt    2700
gttgccattg ctacaggcat cgtggtgtca cgctcgtcgt ttggtatggc ttcattcagc    2760
tccggttccc aacgatcaag gcgagttaca tgatccccca tgttgtgcaa aaaagcggtt    2820
agctccttcg gtcctccgat cgttgtcaga agtaagttgg ccgcagtgtt atcactcatg    2880
gttatggcag cactgcataa ttctcttact gtcatgccat ccgtaagatg cttttctgtg    2940
actggtgagt actcaaccaa gtcattctga gaatagtgta tgcggcgacc gagttgctct    3000
tgcccggcgt caatacggga taataccgcg ccacatagca gaactttaaa agtgctcatc    3060
attggaaaac gttcttcggg gcgaaaactc tcaaggatct taccgctgtt gagatccagt    3120
tcgatgtaac ccactcgtgc acccaactga tcttcagcat cttttacttt caccagcgtt    3180
tctgggtgag caaaaacagg aaggcaaaat gccgcaaaaa agggaataag ggcgacacgg    3240
aaatgttgaa tactcatact cttccttttt caatattatt gaagcattta tcagggttat    3300
tgtctcatga gcggatacat atttgaatgt atttagaaaa ataaacaaat aggggttccg    3360
cgcacatttc cccgaaaagt gccacctgac gtctaagaaa ccattattat catgacatta    3420
acctataaaa ataggcgtat cacgaggccc tttcgtcttc ac                       3462
```

<210> SEQ ID NO 11
<211> LENGTH: 363
<212> TYPE: DNA
<213> ORGANISM: Unknown Organism
<220> FEATURE:
<223> OTHER INFORMATION: Description of Unknown Organism: DNA sequence, human procalcitonin

<400> SEQUENCE: 11

```
ggatccgcac cattcaggtc tgccctggag agcagcccag cagacccggc cacgctcagt      60
gaggacgaag cgcgcctccg gctggctgca ctggtgcagg actatgtgca gatgaaggcc    120
agtgagctgg agcaggagca agagagagag ggctccagcc tggacagccc cagatctaag    180
cggtgcggta atctgagtac ttgcatgctg gcacataca cgcaggactt caacaagttt     240
cacacgttcc cccaaactgc aattggggtt ggagcacctg gaaagaaaag ggatatgtcc    300
agcgacttgg agagagacca tcgccctcat gttagcatgc cccagaatgc caactaaaag    360
ctt                                                                   363
```

```
<210> SEQ ID NO 12
<211> LENGTH: 351
<212> TYPE: DNA
<213> ORGANISM: Unknown Organism
<220> FEATURE:
<223> OTHER INFORMATION: Description of Unknown Organism: DNA sequence,
      human procalcitonin

<400> SEQUENCE: 12
gcaccattca ggtctgccct ggagagcagc ccagcagacc cggccacgct cagtgaggac      60
gaagcgcgcc tcctgctggc tgcactggtg caggactatg tgcagatgaa ggccagtgag     120
ctggagcagg agcaagagag agagggctcc agcctggaca gccccagatc taagcggtgc     180
ggtaatctga gtacttgcat gctgggcaca tacacgcagg acttcaacaa gtttcacacg     240
ttcccccaaa ctgcaattgg ggttggagca cctggaaaga aaagggatat gtccagcgac     300
ttggagagag accatcgccc tcatgttagc atgccccaga atgccaacta a              351
```